(12) United States Patent
    Brown et al.

(10) Patent No.: US 9,347,890 B2
(45) Date of Patent: May 24, 2016

(54) LOW-NOISE SENSOR AND AN INSPECTION SYSTEM USING A LOW-NOISE SENSOR

(71) Applicant: KLA-Tencor Corporation, Milpitas, CA (US)

(72) Inventors: David L. Brown, Los Gatos, CA (US); Yung-Ho Chuang, Cupertino, CA (US); John Fielden, Los Altos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/273,424

(22) Filed: May 8, 2014

(65) Prior Publication Data
    US 2015/0177159 A1    Jun. 25, 2015

Related U.S. Application Data

(60) Provisional application No. 61/918,108, filed on Dec. 19, 2013.

(51) Int. Cl.
    *G01N 21/88*   (2006.01)
    *G01N 21/95*   (2006.01)
    *G01N 21/956*  (2006.01)
    *H01L 31/02*   (2006.01)

(52) U.S. Cl.
    CPC ........ *G01N 21/8851* (2013.01); *G01N 21/9501* (2013.01); *G01N 21/956* (2013.01); *H01L 31/02* (2013.01); *G01N 2021/95676* (2013.01)

(58) Field of Classification Search
    CPC . G01N 2021/458; G01N 21/45; G01N 21/51; G01N 21/6458; G01N 21/956; G01N 21/9501; G01N 2021/95676
    See application file for complete search history.

(56) References Cited

U.S. PATENT DOCUMENTS 3,870,917 A    3/1975   Cuny
3,947,707 A    3/1976   Shannon
                (Continued)

FOREIGN PATENT DOCUMENTS

EP    0746871 B1    5/2000
EP    0602983 B1    6/2000
                (Continued)

OTHER PUBLICATIONS

Hecht, Eugene, Optics, 4th Edition, India: Pearson Education Pte, Ltd. reprint 2004, 4 pages.
                (Continued)

*Primary Examiner* — Tony Ko
(74) *Attorney, Agent, or Firm* — Bever, Hoffman & Harms, LLP

(57) ABSTRACT

A method of inspecting a sample at high speed includes directing and focusing radiation onto a sample, and receiving radiation from the sample and directing received radiation to an image sensor. Notably, the method includes driving the image sensor with predetermined signals. The predetermined signals minimize a settling time of an output signal of the image sensor. The predetermined signals are controlled by a phase accumulator, which is used to select look-up values. The driving can further include loading an initial phase value, selecting most significant bits of the phase accumulator, and converting the look-up values to an analog signal. In one embodiment, for each cycle of a phase clock, a phase increment can be added to the phase accumulator. The driving can be performed by a custom waveform generator.

20 Claims, 13 Drawing Sheets

(56) References Cited

U.S. PATENT DOCUMENTS

| | | | |
|---|---|---|---|
| 4,099,198 A | 7/1978 | Howorth et al. |
| 4,210,922 A | 7/1980 | Shannon |
| 4,275,326 A | 6/1981 | Houtkamp |
| 4,348,690 A | 9/1982 | Jastrzebski |
| 4,467,189 A | 8/1984 | Tsuchiya |
| 4,555,731 A | 11/1985 | Zinchuk |
| 4,760,031 A | 7/1988 | Janesick |
| 5,054,683 A | 10/1991 | Haisma et al. |
| 5,120,949 A | 6/1992 | Tomasetti |
| 5,227,313 A | 7/1993 | Gluck et al. |
| 5,315,126 A | 5/1994 | Field |
| 5,376,810 A | 12/1994 | Hoenk et al. |
| 5,428,392 A | 6/1995 | Castro et al. |
| 5,483,378 A | 1/1996 | Rahn |
| 5,563,702 A | 10/1996 | Emery et al. |
| 5,717,518 A | 2/1998 | Shafer et al. |
| 5,719,069 A | 2/1998 | Sparks |
| 5,731,584 A | 3/1998 | Beyne |
| 5,742,626 A | 4/1998 | Mead et al. |
| 5,760,899 A | 6/1998 | Eismann |
| 5,852,322 A | 12/1998 | Speckbacher |
| 5,940,685 A | 8/1999 | Loomis et al. |
| 5,999,310 A | 12/1999 | Shafer et al. |
| 6,013,399 A | 1/2000 | Nguyen |
| 6,030,852 A | 2/2000 | Sano et al. |
| 6,162,707 A | 12/2000 | Dinh |
| 6,201,601 B1 | 3/2001 | Vaez-Iravani et al. |
| 6,271,916 B1 | 8/2001 | Marxer et al. |
| 6,278,119 B1 | 8/2001 | Nikzad et al. |
| 6,285,018 B1 | 9/2001 | Aebi et al. |
| 6,297,879 B1 | 10/2001 | Yang et al. |
| 6,307,586 B1 | 10/2001 | Costello et al. |
| 6,346,700 B1 | 2/2002 | Cunningham et al. |
| 6,362,484 B1 | 3/2002 | Beyne |
| 6,373,869 B1 | 4/2002 | Jacob |
| 6,403,963 B1 | 6/2002 | Nikzad |
| 6,545,281 B1 | 4/2003 | McGregor |
| 6,608,676 B1 | 8/2003 | Zhao et al. |
| 6,711,283 B1 | 3/2004 | Soenksen |
| 6,837,766 B2 | 1/2005 | Costello |
| 7,005,637 B2 | 2/2006 | Costello et al. |
| 7,039,157 B2 | 5/2006 | Fuji et al. |
| 7,126,699 B1 | 10/2006 | Wihl et al. |
| 7,130,039 B2 | 10/2006 | Vaez-Iravani et al. |
| 7,136,159 B2 | 11/2006 | Tsai et al. |
| 7,141,791 B2 | 11/2006 | Masnaghetti et al. |
| 7,283,166 B1 | 10/2007 | Billman |
| 7,313,155 B1 | 12/2007 | Mu |
| 7,345,825 B2 | 3/2008 | Chuang et al. |
| 7,352,457 B2 | 4/2008 | Kvamme et al. |
| 7,446,474 B2 | 11/2008 | Maldonado |
| 7,465,935 B2 | 12/2008 | Urano et al. |
| 7,471,315 B2 | 12/2008 | Silsby et al. |
| 7,492,510 B2 | 2/2009 | Kuwabara |
| 7,525,649 B1 | 4/2009 | Leong et al. |
| 7,528,943 B2 | 5/2009 | Brown et al. |
| 7,586,108 B2 | 9/2009 | Nihtianov et al. |
| 7,609,303 B1 | 10/2009 | Lee et al. |
| 7,609,309 B2 * | 10/2009 | Brown ............... H04N 5/37206 348/295 |
| 7,714,287 B1 | 5/2010 | James et al. |
| 7,741,666 B2 | 6/2010 | Nozaki et al. |
| 7,750,280 B2 | 7/2010 | Hwang et al. |
| 7,791,170 B2 | 9/2010 | Chiang et al. |
| 7,800,040 B2 | 9/2010 | Blacksberg et al. |
| 7,838,833 B1 | 11/2010 | Lent et al. |
| 7,864,425 B2 | 1/2011 | Okada |
| 7,875,948 B2 | 1/2011 | Hynecek et al. |
| 7,928,382 B2 | 4/2011 | Hatakeyama et al. |
| 7,952,633 B2 | 5/2011 | Brown et al. |
| 7,985,658 B2 | 7/2011 | Lei et al. |
| 7,999,342 B2 | 8/2011 | Hsu et al. |
| 8,017,427 B2 | 9/2011 | Manabe |
| 8,138,485 B2 | 3/2012 | Nihtianov et al. |
| 8,309,443 B2 | 11/2012 | Tanaka et al. |
| 8,450,820 B2 | 5/2013 | Nanver |
| 8,455,971 B2 | 6/2013 | Chen et al. |
| 8,513,587 B2 | 8/2013 | Wang et al. |
| 8,629,384 B1 | 1/2014 | Biellak et al. |
| 2001/0017344 A1 | 8/2001 | Aebi |
| 2001/0024684 A1 | 9/2001 | Steiner et al. |
| 2002/0191834 A1 | 12/2002 | Fishbaine |
| 2003/0222579 A1 | 12/2003 | Habib et al. |
| 2004/0021061 A1 | 2/2004 | Bijkerk |
| 2004/0056279 A1 | 3/2004 | Niigaki |
| 2004/0074261 A1 | 4/2004 | Caron et al. |
| 2004/0227070 A1 | 11/2004 | Bateman et al. |
| 2005/0167575 A1 | 8/2005 | Benz et al. |
| 2005/0196059 A1 | 9/2005 | Inoue et al. |
| 2005/0255625 A1 | 11/2005 | Janesick |
| 2005/0264148 A1 | 12/2005 | Maldonado et al. |
| 2005/0287479 A1 | 12/2005 | Moon |
| 2006/0054778 A1 | 3/2006 | Suhling |
| 2006/0055321 A1 | 3/2006 | Maldonado et al. |
| 2006/0069460 A1 | 3/2006 | Smith et al. |
| 2006/0170324 A1 | 8/2006 | Machuca |
| 2006/0188869 A1 | 8/2006 | Zeskind et al. |
| 2007/0002465 A1 | 1/2007 | Chuang et al. |
| 2007/0023770 A1 | 2/2007 | Miyajima et al. |
| 2007/0034987 A1 | 2/2007 | Costello et al. |
| 2007/0064135 A1 | 3/2007 | Brown et al. |
| 2007/0072326 A1 | 3/2007 | Zheng et al. |
| 2007/0103769 A1 | 5/2007 | Kuwabara |
| 2007/0138378 A1 | 6/2007 | Chang |
| 2007/0177289 A1 | 8/2007 | Shim et al. |
| 2007/0210395 A1 | 9/2007 | Maruyama et al. |
| 2007/0291810 A1 | 12/2007 | Luo et al. |
| 2008/0044932 A1 | 2/2008 | Samoilov et al. |
| 2008/0182092 A1 | 7/2008 | Bondokov |
| 2008/0267241 A1 | 10/2008 | Brown et al. |
| 2008/0315092 A1 | 12/2008 | Kley |
| 2008/0315121 A1 | 12/2008 | Nihtianov et al. |
| 2009/0021717 A1 | 1/2009 | Nihtianov et al. |
| 2009/0091752 A1 | 4/2009 | Terasawa et al. |
| 2009/0125242 A1 * | 5/2009 | Choi ...................... G01N 21/45 702/19 |
| 2009/0128912 A1 | 5/2009 | Okada |
| 2009/0168152 A1 | 7/2009 | Gelernt et al. |
| 2009/0180176 A1 | 7/2009 | Armstrong et al. |
| 2010/0026865 A1 | 2/2010 | Tivarus et al. |
| 2010/0038540 A1 | 2/2010 | Hannebauer |
| 2010/0102213 A1 | 4/2010 | Garris |
| 2010/0140675 A1 | 6/2010 | Rhodes |
| 2010/0148667 A1 | 6/2010 | Niigaki et al. |
| 2010/0164042 A1 | 7/2010 | Manabe |
| 2010/0188655 A1 | 7/2010 | Brown et al. |
| 2010/0208979 A1 | 8/2010 | Abbott et al. |
| 2010/0301437 A1 | 12/2010 | Brown et al. |
| 2011/0062499 A1 | 3/2011 | Burke |
| 2011/0073982 A1 | 3/2011 | Armstrong et al. |
| 2011/0101219 A1 | 5/2011 | Uchiyama et al. |
| 2011/0116077 A1 | 5/2011 | Chuang et al. |
| 2011/0168886 A1 | 7/2011 | Shadman et al. |
| 2011/0169116 A1 | 7/2011 | Nanver et al. |
| 2011/0234790 A1 | 9/2011 | True |
| 2011/0256655 A1 | 10/2011 | Nikzad et al. |
| 2011/0261354 A1 | 10/2011 | Sinfield |
| 2011/0291109 A1 | 12/2011 | Wraback |
| 2012/0012811 A1 | 1/2012 | DeFlumere |
| 2012/0012957 A1 | 1/2012 | Larsen |
| 2012/0081684 A1 | 4/2012 | Den Oef et al. |
| 2012/0132823 A1 | 5/2012 | Menge |
| 2012/0160993 A1 | 6/2012 | Nevet |
| 2012/0170021 A1 | 7/2012 | Walsh |
| 2012/0228485 A1 | 9/2012 | Iwakiri et al. |
| 2012/0268722 A1 | 10/2012 | Nihtianov et al. |
| 2013/0016346 A1 | 1/2013 | Romanovsky et al. |
| 2013/0017205 A1 | 1/2013 | Giaccia et al. |
| 2013/0056843 A1 | 3/2013 | Lee |
| 2013/0082241 A1 | 4/2013 | Kub et al. |
| 2013/0148112 A1 | 6/2013 | Chuang et al. |
| 2013/0149807 A1 | 6/2013 | Jangjan et al. |
| 2013/0176552 A1 | 7/2013 | Brown et al. |
| 2013/0194445 A1 | 8/2013 | Brown et al. |

(56) References Cited

U.S. PATENT DOCUMENTS

| | | |
|---|---|---|
| 2013/0264481 A1 | 10/2013 | Chern et al. |
| 2013/0270663 A1 | 10/2013 | Lin et al. |
| 2013/0313440 A1 | 11/2013 | Chuang et al. |
| 2013/0320211 A1 | 12/2013 | Park et al. |
| 2013/0341504 A1 | 12/2013 | Neill et al. |
| 2014/0034816 A1 | 2/2014 | Chuang et al. |
| 2014/0111799 A1 | 4/2014 | Lei et al. |
| 2014/0151552 A1 | 6/2014 | Jiang et al. |
| 2014/0158864 A1 | 6/2014 | Brown et al. |
| 2014/0203386 A1 | 7/2014 | Bui |
| 2014/0204963 A1 | 7/2014 | Chuang et al. |
| 2014/0246595 A1 | 9/2014 | Menge |
| 2014/0291493 A1 | 10/2014 | Chuang |
| 2014/0362203 A1* | 12/2014 | Delaney ............... H04N 5/2354 348/79 |
| 2015/0200216 A1 | 7/2015 | Muramatsu et al. |
| 2015/0275393 A1 | 10/2015 | Bondokov et al. |
| 2015/0294998 A1 | 10/2015 | Nihtianov |

FOREIGN PATENT DOCUMENTS

| | | |
|---|---|---|
| EP | 1939917 A2 | 7/2008 |
| EP | 2346094 A1 | 7/2011 |
| JP | 10171965 A | 6/1998 |
| JP | 2004031452 A | 1/2004 |
| JP | 2009117454 A | 5/2009 |
| KR | 100688497 | 3/2007 |
| KR | 100826407 | 5/2008 |
| RU | 2297070 C2 | 4/2007 |
| WO | 9532518 A1 | 11/1995 |
| WO | 9617372 A1 | 6/1996 |
| WO | 2007-035858 A2 | 3/2007 |
| WO | 2011091159 A1 | 7/2011 |
| WO | 2014067754 A1 | 5/2014 |

OTHER PUBLICATIONS

Hecht: "Optics", 2nd Edition, Adelphi University, 1987, Addison-Wesley Publishing Co., Inc., 3 pages.

Mouchart et al., "Thin Film Optical Coatings. 7: Two Layer Coatings Close to Antireflection", Applied Optics, vol. 18, No. 8, Apr. 15, 1979, pp. 1226-1232.

Tobin, Kenneth W., "Inspection in Semiconductor Manufacturing", Webster's Encyclopedia of Electrical and Electronic Engineering, vol. 10, pp. 242-262, Wiley & Sons, NY, NY, 1999.

International Search Report and Written Opinion dated Mar. 31, 2014 for PCT/US2013/074124 (P3725-PCT), filed Dec. 10, 2013 in the name of KLA-Tencor Corporation.

Sobieski, Stanley, "Intensified Charge Coupled Devices for Ultra Low Light Level Imaging", NASA, Goddard Space Flight Center, SPIE vol. 78 (1976) Low Light Level Devices, pp. 73-77.

Nanver, Lis K. et al. "Pure-Boron Chemical-Vapor-Deposited Layers: a New Material for Silicon Device Processing", 18th IEEE International Conference on Advanced Thermal Processing of Semiconductors (RTP), Sep. 28, 2010-Oct. 1, 2010, pp. 136-139.

Nanver, Lis K. "Silicon Photodiodes for Low Penetration Depth Beams such as DUV/VUV/EUV Light and Low-Energy Electrons", Advances in Photodiodes, G. Betta, ed., Mar. 22, 2011, pp. 205-224, www.intechopen.com.

Sarubbi, F. et al. "Chemical Vapor Deposition of α-Boron Layers on Silicon for Controlled Nanometer-Deep p+ n Junction Formation", J. Electron. Mat., vol. 39, No. 2, Feb. 2010, pp. 162-173.

Certified priority document U.S. Appl. No. 61/720,700, filed Oct. 31, 2012 corresponding to PCT/EP2013/071080 filed Oct. 9, 2013, pp. 1-44.

Nikzad, Shouleh et al., Delta-doped CCDs: High QE with long-term stability at UV and visible wavelengths, SPIE vol. 2198 (1994), pp. 907-915.

Vaillant, Joel et al., International Conference on Space Optics, High performance UV anti-reflection coating for back thinned CCD and CMOS image sensors, Oct. 4-8, 2010, 4 pages http://www.congrexprojects.com/custom/icso/Papers/TPosters/15_VAILLANT_ICSO_UV.pdf.

Martinelli, Ramon U. "Infrared Photoemission from Silicon", Applied Physics Letters, vol. 16, No. 7, Apr. 1, 1970, pp. 261-262.

Martinelli, Ramon U. "Reflection and Transmission Secondary Emission from Silicon", Applied Physics Letters, vol. 17, No. 8, Oct. 15, 1970, pp. 313-314.

Henderson, Brian S. "Study of Negative Electron Affinity GaAs Photocathodes", Department of Physics and Astronomy, Rice University, Houston, TX, Aug. 7, 2009, 18 pages.

Allen, F. G. et al. "Work Function, Photoelectric Threshold, and Surface States of Atomically Clean Silicon", Physical Review, vol. 127, No. 1, Jul. 1, 1962, pp. 150-158.

Howorth, J. R. et al. "Transmission silicon photoemitters and electron multipliers," Journal of Physics D: Applied Physics, vol. 9, No. 5, Apr. 1, 1976, pp. 785-794.

Fu et al. "Optimizing GaN photocathode structure for higher quantum efficiency", Optik, vol. 123, No. 9, May 2012, pp. 756-768.

Janesick, J. R. "Scientific Charge-Coupled Devices", SPIE Press, 2001, pp. 556-561.

Lim, Seunghyun; "Low-Power Analog-to-Digital Concerters for High-Speed DMOS Image Sensor", Graduate School, Yonsei University Dept. of Electrical and Electronic Engineering, Feb. 2010, pp. 16-21 (http://ww.riss.kr/link?id=T119950925).

Sarubbi F et al: "Pure boron-doped photodiodes: a solution for radiation detection in EUV lithography", Proceedings of the 38th European Solid-State Device Research Conference: Edinburgh International Conference Centre, Endiburgh, Scotland, UK, Sep. 15-19, 2008, Piscataway, NJ: IEEE, US, Sep. 15, 2008, pp. 278-281.

KLA-Tencor Corporation; PCT International Search Report dated Dec. 8, 2015 for Application No. PCT/US2015/047307, 3 pages.

KLA-Tencor Corporation; PCT International Search Report dated Dec. 29, 2015 for Application No. PCT/US2015/051538, 3 pages.

Fu, Xiaoqian, "Higher Quantum Efficiency by Optimizing GaN Photocathode Structure", 978-1-4244-6644-3/10/©2010 IEEE, pp. 234-235.

Huang, Qiyu et al., "Back-Side Illuminated Photogate CMOS Active Pixel Sensor Structure With Improved Short Wavelength Response", IEEE Sensors Journal, vol. 11, No. 9, Sep. 2011, 5 pages.

Itzler, Mark et al., "InP-based Geiger-mode avalanche photodiode arrays for three-dimensional imaging at 1.06 μm", Proceedings of SPIE, vol. 7320 (2000), 12 pages.

Niclass, Cristiano et al., "Design and Characterization of a CMOS 3-D Image Sensor Based on Single Photon Avalanche Diodes", IEEE Journal of Solid-State Circuits, vol. 40, No. 9, Sep. 2005, 8 pages.

Paetzel, Rainer et al., "Activation of Silicon Wafer by Excimer Laser" 18th IEEE Conf. Advanced Thermal processing of Semiconductors—RTP 2010, 5 pages.

Stevanovic, Nenad et al., "A CMOS Image Sensor for High-Speed Imaging", 2000 IEEE Int'l. Conference Solid-State Circuits, 3 pages.

Dulinski, Wojciech et al., "Tests of a backside illuminated monolithic CMOS pixel sensor in an HPD set-up", Nuclear Instruments and Methods in Physics Research A 546 (2005) 274-280, 7 pages.

* cited by examiner

LOW-NOISE SENSOR AND AN INSPECTION SYSTEM USING A LOW-NOISE SENSOR

RELATED APPLICATIONS

The present application claims priority to U.S. Provisional Patent Application 61/918,108, entitled "System And Method For Clocking A Low-Noise Sensor And An Inspection System And Method Using A Low-Noise Sensor", and filed on Dec. 19, 2013. This application is incorporated by reference herein.

The present application is related to U.S. patent application Ser. No. 13/364,308, entitled "High-density digitizer", filed on Feb. 1, 2012, U.S. Provisional Application 61/735,427, entitled "Method and apparatus for high speed acquisition of moving images using pulsed illumination", filed on Dec. 10, 2012, U.S. patent application Ser. No. 13/710,315, entitled "Electron-bombarded charge-coupled device and inspection systems using EBCCD detectors", filed on Dec. 10, 2012, U.S. patent application Ser. No. 13/792,166, entitled "Back-illuminated sensor with boron layer", filed on Mar. 10, 2013, U.S. patent application Ser. No. 13/947,975, entitled "Photocathode including silicon substrate with boron layer", filed on Jul. 22, 2013, U.S. Published Patent Application 2010/0188655, entitled, "TDI sensor modules with localized driving and signal processing circuitry for high speed inspection", filed on Oct. 7, 2009, U.S. Published Patent Application 2010/0301437, entitled "Anti-reflective coating for sensors suitable for high throughput inspection systems", filed on Jun. 1, 2009, U.S. Published Patent Application 2011/0073982, entitled "Inspection system using back side illuminated linear sensor", filed on May 25, 2007, U.S. Pat. No. 7,609,309, entitled "Continuous clocking of TDI sensors", issued on Oct. 27, 2009, and U.S. Pat. No. 7,952,633, entitled "Apparatus for continuous clocking of TDI sensors", issued on May 31, 2011. These applications and patents are incorporated by reference herein.

BACKGROUND OF THE DISCLOSURE

1. Field of the Disclosure

The present application relates to image sensors and associated electronic circuits suitable for sensing radiation at visible, UV, deep UV (DUV), vacuum UV (VUV), and extreme UV (EUV) wavelengths, and to methods for operating such image sensors. The sensors and circuits are particularly suitable for use in inspection systems, including those used to inspect photomasks, reticles, and semiconductor wafers.

2. Related Art

The integrated circuit industry requires inspection tools with increasingly higher sensitivity to detect ever smaller defects and particles whose sizes may be smaller than 20 nm. Those same inspection tools need to be capable of detecting large defects such as scratches and water marks, which may have dimensions ranging from less than 1 μm to multiple mm, and of measuring the surface roughness or haze which may have peak-to-valley amplitudes of a few nm or less than 1 nm. The inspection tools must also be able to detect defects and particles on, or within, high-reflectivity and low-reflectivity patterns and films.

Small particles, small defects, low contrast defects, and low-amplitude roughness scatter light only very weakly. To detect small defects or particles on photomasks, reticles, and semiconductor wafers, low-noise sensors with low-noise driving and readout electronics are required. The noise level of the signal depends on the intrinsic noise level of the sensor, on the noise level of the readout electronics, and on the amount of noise that is coupled into the signals from internal and external sources, including the clock signals driving the sensor and associated electronics.

U.S. Pat. No. 7,609,309, entitled "Continuous clocking of TDI sensors", issued on Oct. 27, 2009 and U.S. Pat. No. 7,952,633, entitled "Apparatus for continuous clocking of TDI sensors", issued on May 31, 2011 describe waveforms that are useful for driving the clocks of low-noise CCD sensors. The '633 patent further describes a circuit using an FPGA, digital-to-analog converters (DACs), filters, and power drivers or buffers for generating those waveforms and driving a CCD sensor. Multiple integrated circuits are required to implement such a circuit. For CCD sensors with one million or more pixels and tens or hundreds of output channels, many integrated circuits and a large circuit board area would be needed to implement such a circuit. This implementation would result in some of the signals having to travel long (e.g. multi-cm) distances to the sensor, thereby making it difficult to control noise, cross talk, and ground return currents well enough to enable low-level signal detection from the sensor.

An important limitation of prior art CCD sensors and driving circuits can be appreciated by referring to FIG. 11, which illustrates the timing of a signal readout from a CCD. FIG. 11 shows the waveform of output voltage 1110 and the waveform of reset clock 1101, both as a function of time. The reset clock resets the output voltage after one pixel so that the next pixel can be output. When the reset clock 1101 is high (positive) as indicated by arrow 1102, the output charge from the prior pixel is discharged so that the output signal settles down to a reset level indicated by the waveform at arrow 1115.

Output voltage 1110 illustrates several practical issues that can degrade the signal-to-noise ratio and accuracy of the output signal of CCD image sensors, particularly when the sensor is operated at high speed as is required for inspection and metrology applications in semiconductor and related industries. When the reset clock 1101 switches from a low voltage to a high voltage as shown by the waveform at arrow 1103, some of that voltage swing is coupled to the output voltage because the reset transistor is necessarily physically located on the CCD adjacent to the output sensing node. This coupling destabilizes the output voltage 1110 as indicated by the waveform at arrow 1112.

Furthermore, when the reset clock 1101 goes low as indicated by the waveform at arrow 1104, that high-to-low transition is similarly coupled to the output voltage and destabilizes it as indicated by the waveform at arrow 1114. After a little time, the output voltage 1110 settles down and stabilizes at the reset level indicated by the waveform at 1115. When the signal from a pixel is transferred to the output, the output voltage decreases from the reset level to a lower level, such as the level indicated by arrow 1117 because the signal comprises electrons and is, hence, a negative charge. In FIG. 11, the level indicated by arrow 1117 represents the output voltage corresponding to a saturated pixel, i.e. a maximum signal, and another level indicated by arrow 1119 represents the output voltage corresponding to a signal that is significantly less than the maximum. Although not shown, typically there will be some settling time after the transition from the reset level of the waveform indicated by arrow 1115 to the signal levels of the waveform indicated by arrows 1117 or 1119.

In FIG. 11, the signal in the first pixel is proportional to the difference between the output voltages at arrows 1117 and 1115, and the signal in the second pixel is proportional to the difference between the output voltages at arrows 1115 and 1119. Usually correlated double sampling is used to measure the difference between the reset voltage at arrow 1115 and the output voltage such as at arrows 1117 and 1119. Correlated double sampling is a well-known technique and is described, for example, by J. R. Janesick, "Scientific Charge-Coupled Devices", SPIE Press, 2001, pp. 556-561.

As can be appreciated from FIG. 11, when the signal needs to be read out at high speed, such as a speed of about 25 MHz or more, there is only a short time for the output voltage 1110 to settle to the reset voltage at arrow 1115 and the signal voltage, such as at arrows 1117 and 1119. For example at 50 MHz, the total time for one pixel is 20 ns. The reset clock pulses must necessarily be much shorter than this time with rise and fall times of, at most, 1-2 ns. Such short pulses with fast rise and fall times necessarily cause significant destabilization of the output voltage. Only a few ns are available for the output voltage to settle. In some cases, the signal may not have enough time to fully stabilize leading to noisy image data.

Therefore, a need arises for an image sensor and associated electronics capable of acquiring image data at high speed with low noise yet overcoming some, or all, of the above disadvantages.

SUMMARY OF THE DISCLOSURE

A method of inspecting a sample at high speed is described. This method includes directing and focusing radiation onto the sample, and receiving radiation from the sample and directing received radiation to an image sensor. The received radiation may be scattered radiation or reflected radiation. Notably, the method includes driving the image sensor with predetermined signals. The predetermined signals minimize a settling time of an output signal of the image sensor. The predetermined signals are generated from look-up values. The sequence of look-up values is determined by a phase accumulator.

The driving can further include loading an initial phase value, selecting most significant bits of the phase accumulator as an address in a look-up table, and converting the corresponding look-up values to an analog signal. In one embodiment, for each cycle of a phase clock, a phase increment can be added to the phase accumulator.

The driving can further include determining whether a maximum phase accumulator value is exceeded. When the maximum phase accumulator value is not exceeded, then the most significant bits (e.g. 16 bits) of the phase accumulator can be selected and the phase increment can be added to the phase accumulator. When the maximum phase accumulator value is exceeded, then a cycle count can be incremented. The driving can further include determining whether a maximum count cycle value is exceeded. When the maximum count cycle value is not exceeded, then selecting the most significant bits as an address in a look-up table and adding the phase increment to the phase accumulator can be repeated. When the maximum count cycle value is exceeded, then the driving can be stopped.

A system for inspecting a sample is also described. This system includes an illumination source, a device configured to perform light detection, optics configured to direct light from the illumination source to the sample and to direct light outputs, reflections, or transmissions from the sample to the device, and a driving circuit. Notably, the driving circuit, which drives the device, includes a custom waveform generator.

The custom waveform generator minimizes a settling time of an output signal of the device. The custom waveform generator includes a phase accumulator for receiving clock and control signals, a look-up table coupled to an output of the phase accumulator, and a digital-to-analog converter coupled to an output of the look-up table.

In one embodiment, the optics includes first and second channel image mode relays. The first channel image mode relay is used when the light outputs, reflections, or transmissions correspond to a first channel. The second channel image mode relay is used when the light outputs, reflections, or transmissions correspond to a second channel. The device may be an image sensor configured to receive relay outputs of the first channel image mode relay and the second channel image mode relay.

In one embodiment, the device may comprise a semiconductor membrane. In another embodiment, the semiconductor membrane may include circuit elements formed on a first surface of the semiconductor membrane and a pure boron layer deposited on a second surface of the semiconductor membrane. In yet another embodiment, the device may comprise an electron bombarded image sensor. In yet another embodiment, the device may include one or more image sensors, such as time delay integration (TDI) sensors. A TDI sensor may have readout circuits on two sides that are used to read out two different signals simultaneously.

The sample may be supported by a stage, which moves relative to the optics during the inspection. When the device is a TDI sensor, the TDI sensor may convert the detected light into an electrical charge. The electrical charges may be shifted within the TDI sensor in synchrony with the motion of the stage.

The exemplary inspection system may include one or more illumination paths that illuminate the sample from different angles of incidence and/or different azimuth angles and/or with different wavelengths and/or polarization states. The exemplary inspection system may include one or more collection paths that collect light reflected or scattered by the sample in different directions and/or are sensitive to different wavelengths and/or to different polarization states.

DETAILED DESCRIPTION OF THE DRAWINGS

Improved sensors for semiconductor inspection systems are described herein. The following description is presented to enable one of ordinary skill in the art to make and use the invention as provided in the context of a particular application and its requirements. As used herein, directional terms such as "top", "bottom", "over", "under", "upper", "upward", "lower", "down", and "downward" are intended to provide relative positions for purposes of description, and are not intended to designate an absolute frame of reference. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed.

Figure 1:
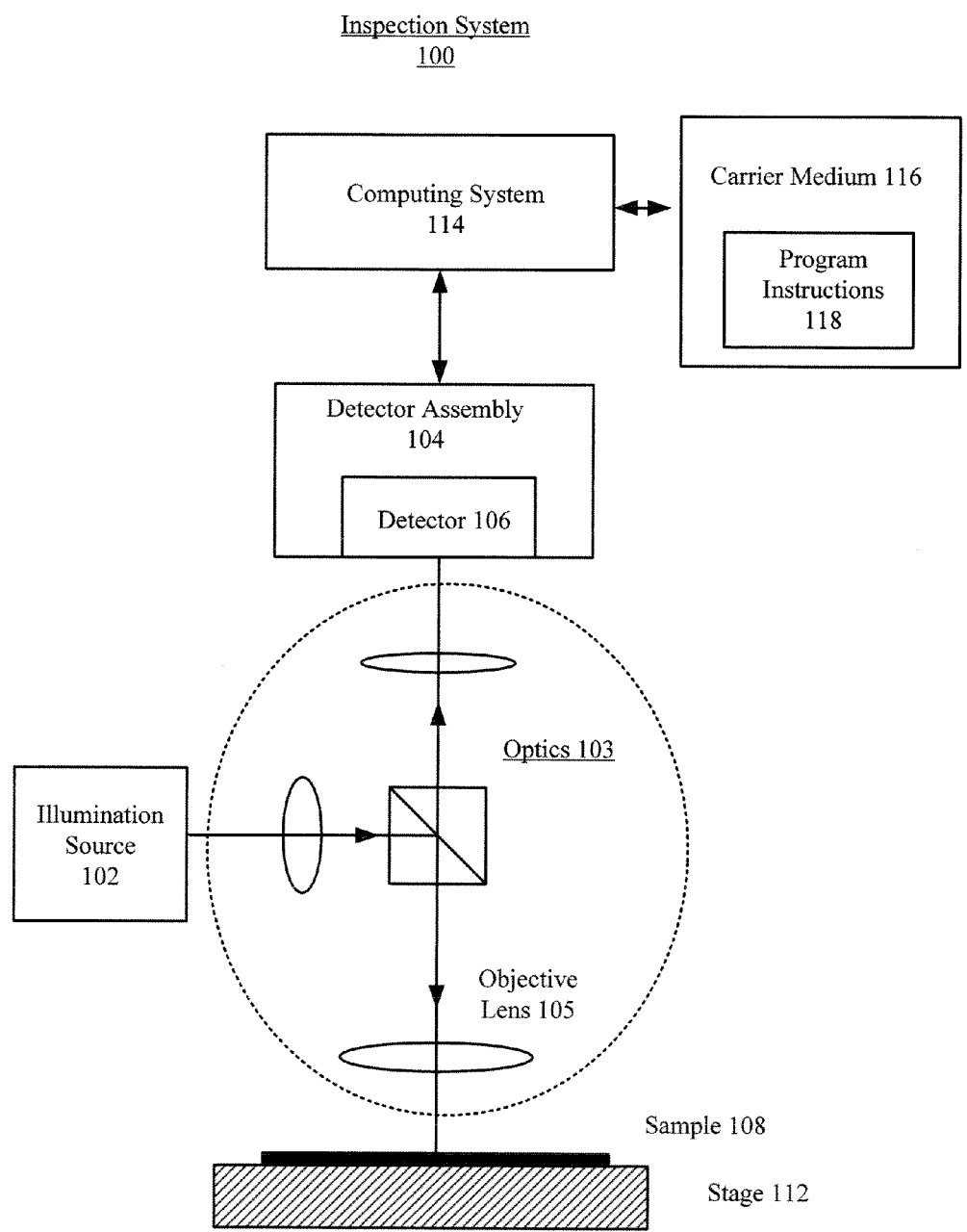
FIG. 1 illustrates an exemplary inspection system.

FIG. 1 illustrates an exemplary inspection system 100 configured to inspect or measure a sample 108, such as a wafer, reticle, or photomask. Sample 108 is placed on a stage 112 to facilitate movement to different regions of sample 108 underneath the optics. Stage 112 may comprise an X-Y stage or an R-θ stage. In some embodiments, stage 112 can adjust the height of sample 108 during inspection to maintain focus. In other embodiments, an objective lens 105 can be adjusted to maintain focus.

An illumination source 102 may comprise one or more lasers and/or a broad-band light source. Illumination source 102 may emit DUV and/or VUV radiation. Optics 103, including an objective lens 105, directs that radiation towards and focuses it on sample 108. Optics 103 may also comprise mirrors, lenses, and/or beam splitters (not shown for simplicity). Light reflected or scattered from sample 108 is collected, directed, and focused by optics 103 onto a detector 106, which is within a detector assembly 104.

Detector assembly 104 includes at least one of the circuits described herein or implements at least one of the methods described herein for driving and/or controlling detector 106. Detector 106 may include a two-dimensional array sensor or a one-dimensional line sensor. In one embodiment, the output of detector 106 is provided to a computing system 114, which analyzes the output. Computing system 114 is configured by program instructions 118, which can be stored on a carrier medium 116.

In one embodiment, illumination source 102 may be a continuous source, such as an arc lamp, a laser-pumped plasma light source, or a CW laser. In another embodiment, illumination source 102 may be a pulsed source, such as a mode-locked laser, a Q-switched laser, or a plasma light source pumped by a Q-switched laser. In one embodiment of inspection system 100 incorporating a Q-switched laser, the image sensor or sensors within detector 106 are synchronized with the laser pulses. In this embodiment, the image sensor may operate in a TDI mode during the laser pulse and then may readout the data through multiple outputs on both sides of the sensor in between laser pulses.

One embodiment of inspection system 100 illuminates a line on sample 108, and collects scattered and/or reflected light in one or more dark-field and/or bright-field collection channels. In this embodiment, detector 106 may include a line sensor or an electron-bombarded line sensor.

Another embodiment of inspection system 100 illuminates multiple spots on sample 108, and collects scattered and/or reflected light in one or more dark-field and/or bright-field collection channels. In this embodiment, detector 106 may include a two-dimensional array sensor or an electron-bombarded two-dimensional array sensor.

Additional details of various embodiments of inspection system 100 are described in U.S. patent application 13/544,954, entitled "Wafer inspection system", filed on Jul. 9, 2012, U.S. Published Patent Application 2009/0180176, entitled "Split field inspection system using small catadioptric objectives", published on Jul. 16, 2009, U.S. Published Patent Application 2007/0002465, entitled "Beam delivery system for laser dark-field illumination in a catadioptric optical system", published on Jan. 4, 2007, U.S. Pat. No. 5,999,310, entitled "Ultra-broadband UV microscope imaging system with wide range zoom capability, issued on Dec. 7, 1999, and U.S. Pat. No. 7,525,649, entitled "Surface inspection system using laser line illumination with two dimensional imaging", issued on Apr. 28, 2009. All of these patents and patent applications are incorporated by reference herein.

Figure 2A:
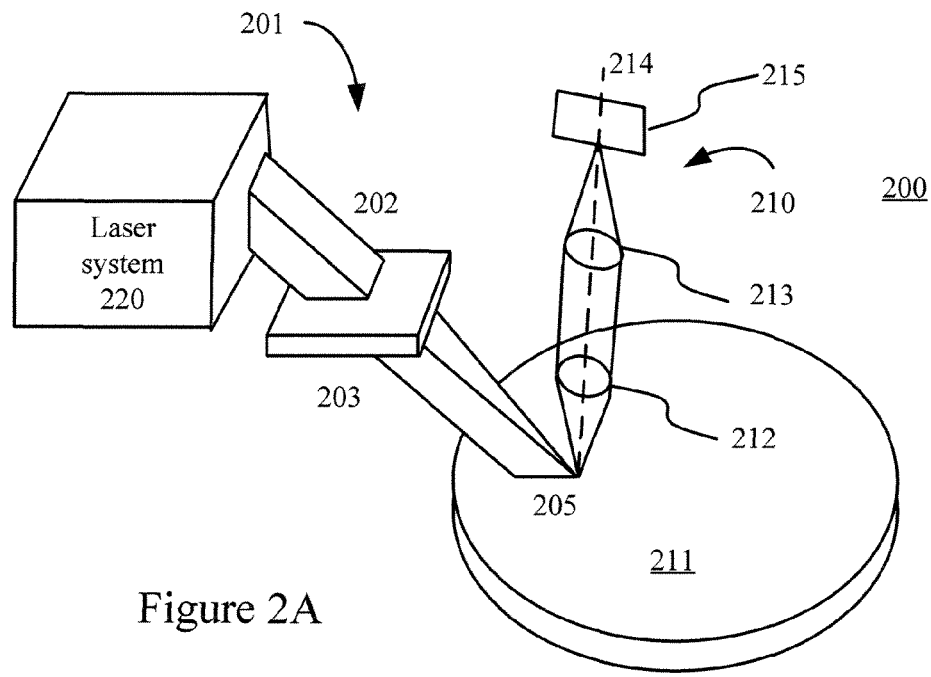
FIGS. 2A and 2B illustrates an exemplary inspection system with line illumination and one or more collection channels.
Figure 2B:
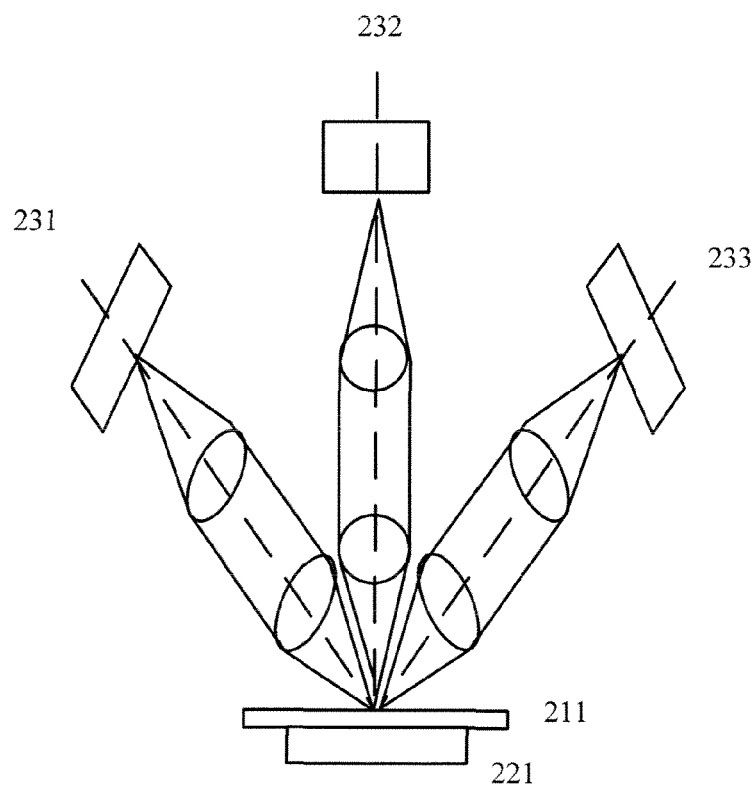

FIGS. 2A and 2B illustrate aspects of dark-field inspection systems that incorporate the circuits and/or methods described herein in accordance with other exemplary embodiments of the present invention. In FIG. 2A, illumination optics 201 comprises a laser system 220, which generates light 202 that is focused by a mirror or lens 203 into a line 205 on surface of a wafer or photomask (sample) 211 being inspected. Collection optics 210 directs light scattered from line 205 to a sensor 215 using lenses and/or mirrors 212 and 213. An optical axis 214 of collection optics 210 is not in the illumination plane of line 205. In some embodiments, optical axis 214 is approximately perpendicular to line 205. Sensor 215 comprises an array sensor, such as a linear array sensor. One or more of the circuits and/or methods described herein are used to drive or control sensor 215.

FIG. 2B illustrates one embodiment of multiple dark-field collection systems 231, 232 and 233, each collection system substantially similar to collection optics 210 of FIG. 2A. Collection systems 231, 232 and 233 may be used in combination with illumination optics substantially similar to illumination optics 201 of FIG. 2A. Each collection system 231, 232 and 233 incorporates one, or more, of the circuits and/or methods described herein to drive and/or control its sensor. Sample 211 is supported on stage 221, which moves the areas to be inspected underneath the optics. Stage 221 may comprise an X-Y stage or an R-θ stage, which preferably moves substantially continuously during the inspection to inspect large areas of the sample with minimal dead time.

More details of inspection systems in accordance with the embodiments illustrated in FIGS. 2A and 2B are described in U.S. Pat. No. 7,525,649, entitled "Surface inspection system using laser line illumination with two dimensional imaging", issued on Apr. 28, 2009. U.S. Pat. No. 6,608,676, entitled "System for detecting anomalies and/or features of a surface", issued on Aug. 19, 2003, and incorporated by reference herein, also describes line illumination systems suitable for inspection of un-patterned or patterned wafers.

Figure 3:
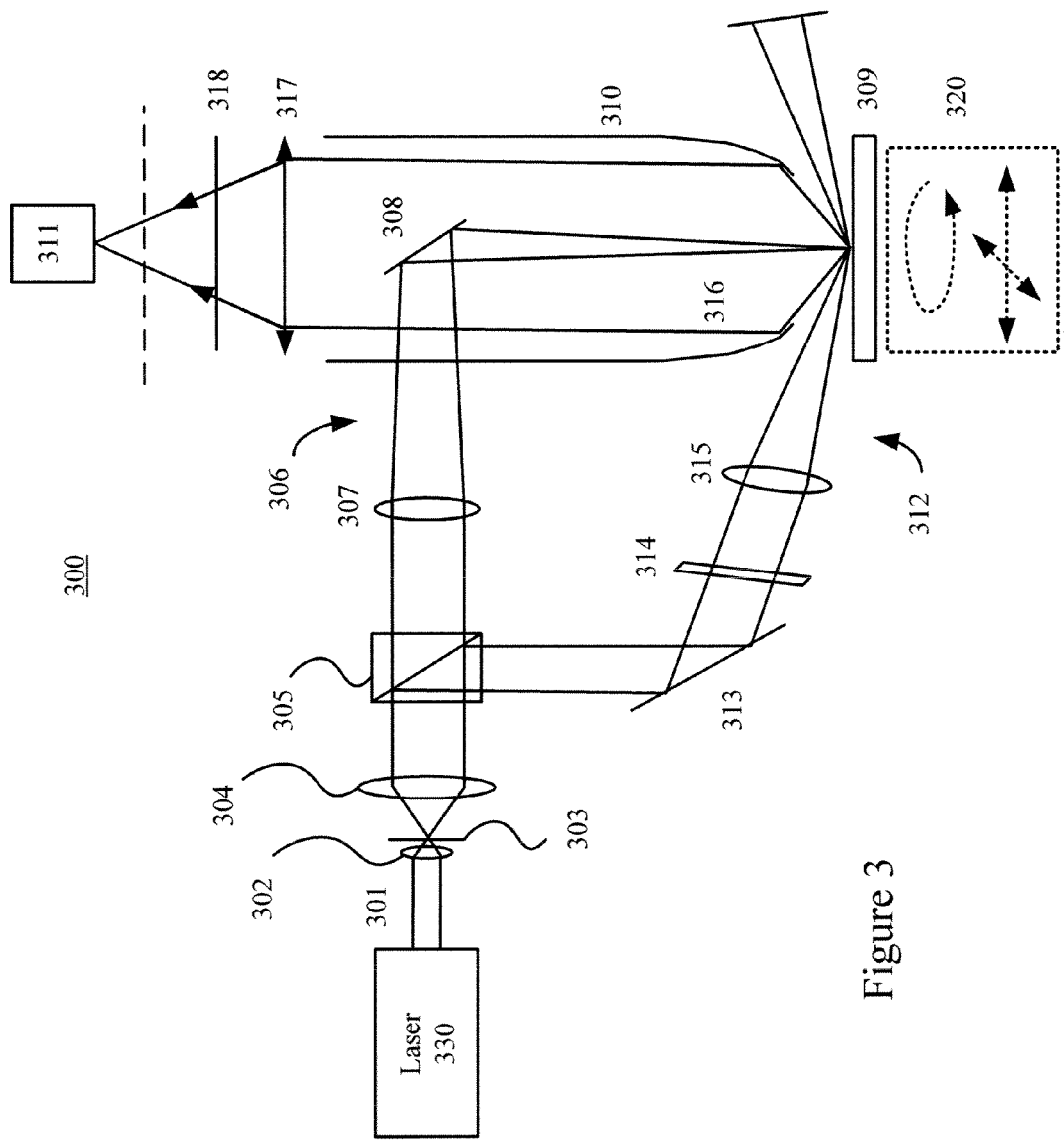
FIG. 3 illustrates an exemplary inspection system with normal and oblique illumination.

FIG. 3 illustrates an inspection system 300 configured to detect particles or defects on a sample using both normal and oblique illumination beams. In this configuration, a laser system 330 provides a laser beam 301. A lens 302 focuses beam 301 through a spatial filter 303. Lens 304 collimates the beam and conveys it to a polarizing beam splitter 305. Beam splitter 305 passes a first polarized component to the normal illumination channel and a second polarized component to the oblique illumination channel, where the first and second components are orthogonal. In a normal illumination channel 306, the first polarized component is focused by optics 307 and reflected by a mirror 308 towards a surface of a sample 309. The radiation scattered by sample 309 (such as a wafer or photomask) is collected and focused by a paraboloidal mirror 310 to a sensor 311.

In an oblique illumination channel 312, the second polarized component is reflected by a beam splitter 305 to a mirror 313 which reflects such beam through a half-wave plate 314 and focused by optics 315 to sample 309. Radiation originating from the oblique illumination beam in oblique channel 312 and scattered by sample 309 is collected by paraboloidal mirror 310 and focused to sensor 311. Sensor 311 and the illuminated area (from the normal and oblique illumination channels on sample 309) are preferably at the foci of paraboloidal mirror 310.

Paraboloidal mirror 310 collimates the scattered radiation from sample 309 into a collimated beam 316. Collimated beam 316 is then focused by an objective 317 and through an analyzer 318 to sensor 311. Note that curved mirrored surfaces having shapes other than paraboloidal shapes may also be used. An instrument 320 can provide relative motion between the beams and sample 309 so that spots are scanned across the surface of sample 309. One or more of the circuits and/or methods described herein are used to drive or control sensor 311. U.S. Pat. No. 6,201,601, entitled "Sample inspection system", issued on Mar. 13, 2001 and incorporated by reference herein, describes inspection system 300 in further detail.

Figure 4:
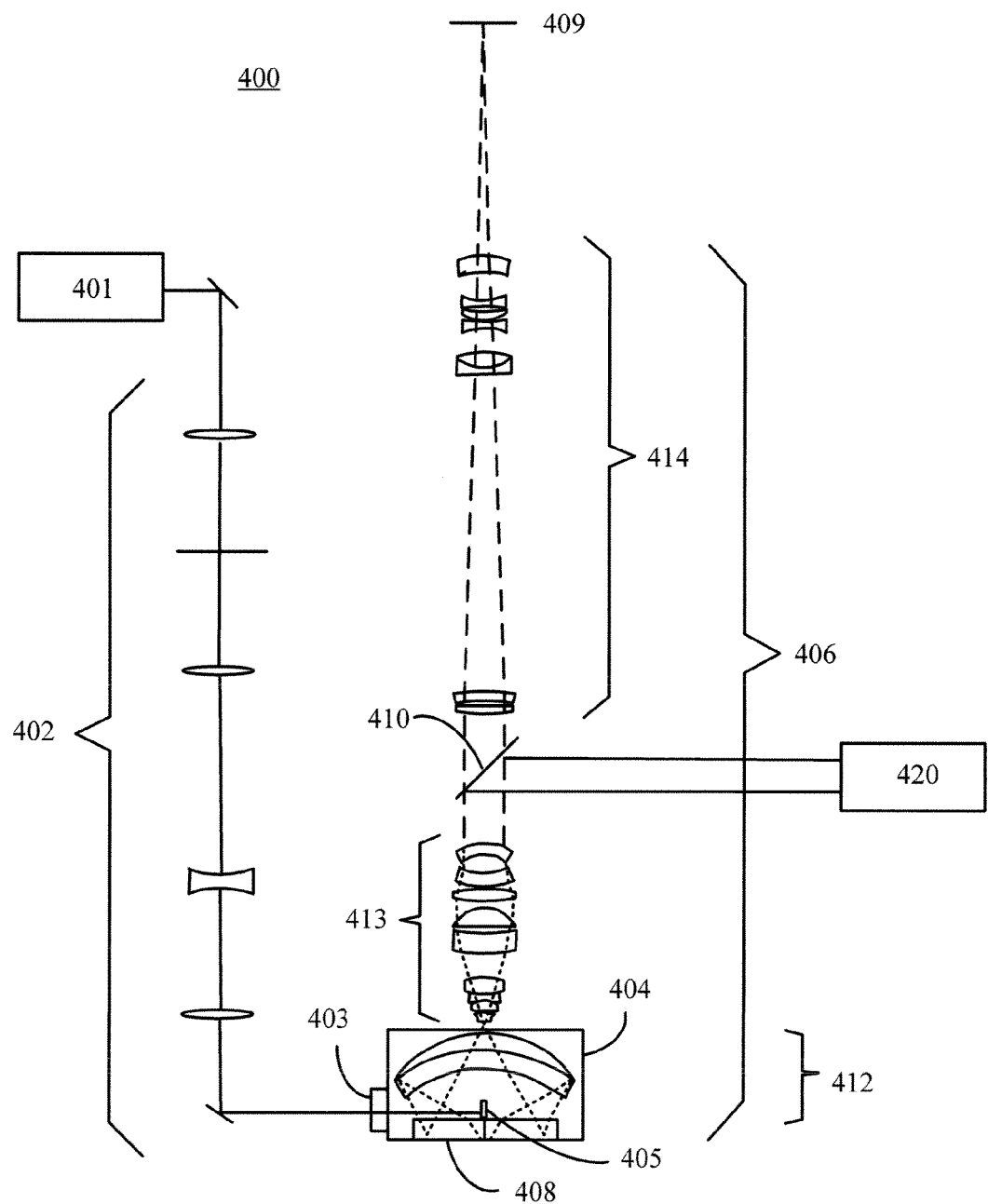
FIG. 4 illustrates an exemplary inspection system with bright-field and dark-field illumination channels.

FIG. 4 illustrates an exemplary catadioptric imaging system 400 configured as an inspection system with bright-field and dark-field inspection modes. System 400 may incorporate two illuminations sources: a laser 401 and a broad-band light illumination module 420.

In a dark-field mode, adaptation optics 402 control the laser illumination beam size and profile on the surface being inspected. A mechanical housing 404 includes an aperture and window 403, and a prism 405 to redirect the laser along the optical axis at normal incidence to the surface of a sample 408. A prism 405 also directs the specular reflection from surface features of sample 408 out of an objective 406. Objective 406 collects light scattered by sample 408 and focuses it on a sensor 409. Lenses for objective 406 can be provided in the general form of a catadioptric objective 412, a focusing lens group 413, and a tube lens section 414, which may, optionally, include a zoom capability. Laser 401 may be a high-repetition-rate pulsed laser, such as a mode locked laser, or a CW laser.

In a bright-field mode, a broad-band illumination module 420 directs broad-band light to a beam splitter 410, which reflects that light towards focusing lens group 413 and catadioptric objective 412. Catadioptric objective 412 illuminates sample 408 with the broadband light. Light that is reflected or scattered from the sample is collected by objective 406 and focused on sensor 409. Broad-band illumination module 420 comprises, for example, a laser-pumped plasma light source or an arc lamp. Broad-band illumination module 420 may also include an auto-focus system to provide a signal to control the height of sample 408 relative to catadioptric objective 412.

One or more of the circuits and/or methods described herein are used to drive or control sensor 409. Published Patent Application 2007/0002465, entitled "Beam delivery system for laser dark-field illumination in a catadioptric optical system", published on Jan. 4, 2007 and incorporated by reference herein, describes system 400 in further detail.

Figure 5A:
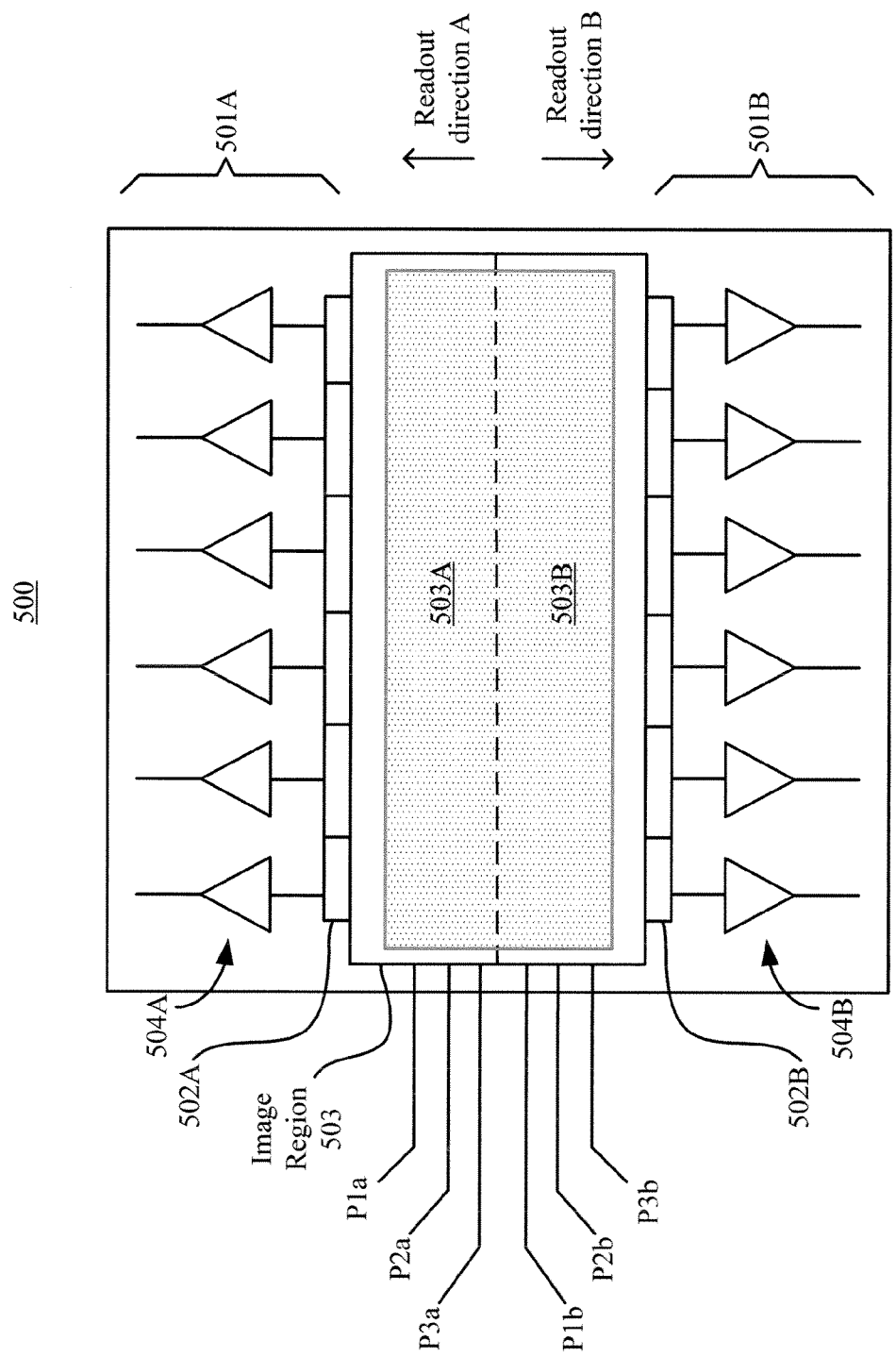
FIG. 5A illustrates an exemplary split-readout image sensor including two sets of readout circuits that may be used with the systems, circuits, and methods described herein.

FIG. 5A illustrates an exemplary split-readout image sensor 500 that is used in some embodiments of the invention disclosed herein. Image sensor 500 includes two sets of readout circuits 501A and 501B positioned on opposite sides of an image region 503. Image region 503 may include a pure boron layer on its light sensitive surface. Readout circuits 501A and 501B can include serial registers 502A and 502B and readout amplifiers 504A and 504B, as well as other components such as transfer gates. Exemplary embodiments of readout circuits 501A and 501B, as well as other components of sensor 500 are described in U.S. Pat. No. 7,609,309, entitled "Continuous Clocking of TDI Sensors", issued Oct. 27, 2009, which is incorporated by reference herein. Image region 503 comprises a two-dimensional (2D) array of pixels arranged in columns such that the pixels in the columns in region 503A can be transferred in readout direction A, and the pixels in the columns in region 503B can be transferred in readout direction B. The top row of region 503A and the bottom row of region 503B can be read out concurrently into serial registers 502A and 502B, respectively. Each row is then read out one pixel at a time in the simplest case. In preferred embodiments, the serial registers 502A and 502B can be divided into a plurality of register segments (e.g. FIG. 5A shows each serial register being divided into six segments), thereby allowing parallel read out using a plurality of amplifiers 504A and 504B.

Notably, readout circuits 501A and 501B can be operated independently, thereby allowing image sensor 500 to provide two readout directions A and B. In a split-readout mode, each side of image region 503 (i.e. sides 503A and 503B) can be synchronously clocked to read out one image row into their respective output channels. In one embodiment, image region 503 may have 1000 rows, each row formed by multiple pixels. Therefore, during the split-readout mode, 500 rows could be read out in direction A and, concurrently, 500 rows could be read out in direction B.

Figure 5B:
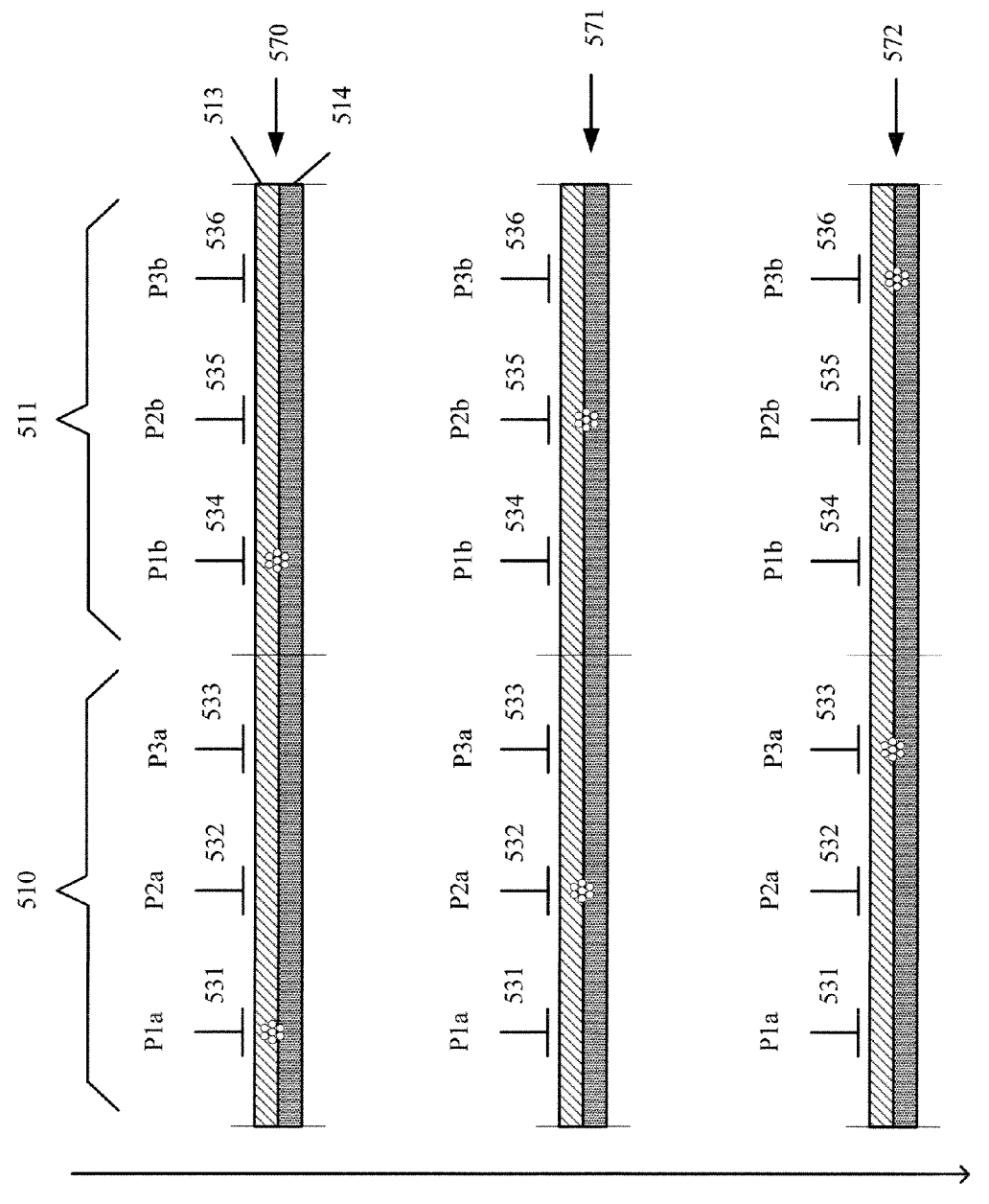
FIG. 5B illustrates the operation of a split-readout image sensor such as that shown in FIG. 5A.

This split-readout mode is possible based on the timed activation of charge-coupled device (CCD) drivers in the image sensor. For example, a plurality of CCD clock signals P1a, P2a, P3a, P1b, P2b, and P3b can be used to control the transfer of charges within the image region 503. Although 3 clock signals per pixel are shown in this exemplary sensor, CCD designs are known in the art for 2, 3 and 4 phase clocks. 2 or 4 phase clocks may be used in alternative embodiments of this invention. As shown in FIG. 5B, CCD clocks P1a, P2a, P3a, P1b, P2b, and P3b can be characterized as driving sets of gate electrodes (hereinafter gates). In one preferred embodiment of the image sensor, three gates are provided for each pixel to provide three phases. In FIG. 5B, two pixels 510 and 511 are shown, wherein gates 531, 532, and 533 are positioned over pixel 510 and gates 534, 535, and 536 are positioned over pixel 511. In the image sensor, pixels 510 and 511 are aligned along the read-out axis to form part of a column of the 2D array of pixels forming image region 503.

Image region 503 can be implemented as an optical sensor or a charged particle sensor. In one optical sensor embodiment, image region 503 can include a photo-sensitive p-type silicon substrate 514 and an n-type buried channel 513. The electrostatic forces in silicon substrate 514 are determined by the voltage level applied to a particular gate by a clock input signal (e.g. one of clock signals P1a, P2a, P3a, P1b, P2b, and P3b). High voltages induce the formation of a potential "well" beneath the gate, whereas low voltages form a potential barrier to electron movement. To ensure that charge from one pixel is not mixed with other pixels, a gate voltage is driven high when an adjacent gate voltage is driven low. At an initial state at time 570, gates 531 and 534 of pixels 510 and 511, respectively, have high level voltages that form potential wells that collect and hold the integrated charges (i.e. electrons), and gates 532, 533 (of pixel 510) and 535, 536 (of pixel 511) have low level voltages that form potential barriers. At a subsequent time 571, gates 532 and 535 of pixels 510 and 511, respectively, have high level voltages that form potential wells that collect and hold the integrated charges, and gates 531, 533 (of pixel 510) and 534, 536 (of pixel 511) have low level voltages that form potential barriers. At yet a subsequent time 572, gates 533 and 536 of pixels 510 and 511, respectively, have high level voltages that form potential wells with integrated charge (i.e. electrons), and gates 531, 532 (of pixel 510) and 534, 535 (of pixel 511) have low level voltages that form potential barriers. Note that adjacent gates when shifting charge preferably both have a high level voltage for a short time to facilitate charge transfer. Thus, from time 570 to time 571, the charge is shifted from left to right, i.e. from pixel 510 to pixel 511. A similar directional shifting of charge takes place from time 571 to time 572. By using separate clocks in regions 503A and 503B of FIG. 5A, the direction of transfer can be independently controlled in the two regions.

Additional details of split-readout image sensor 500 are provided in U.S. patent application Ser. No. 14/096,911, entitled "Method and apparatus for high speed acquisition of moving images using pulsed illumination", filed on Dec. 4, 2013, and incorporated by reference herein. Additional details regarding other exemplary image sensors are provided in U.S. Pat. No. 7,528,943, entitled "Method and apparatus for simultaneous high-speed acquisition of multiple images", issued May 5, 2009, and incorporated by reference herein.

Figure 6:
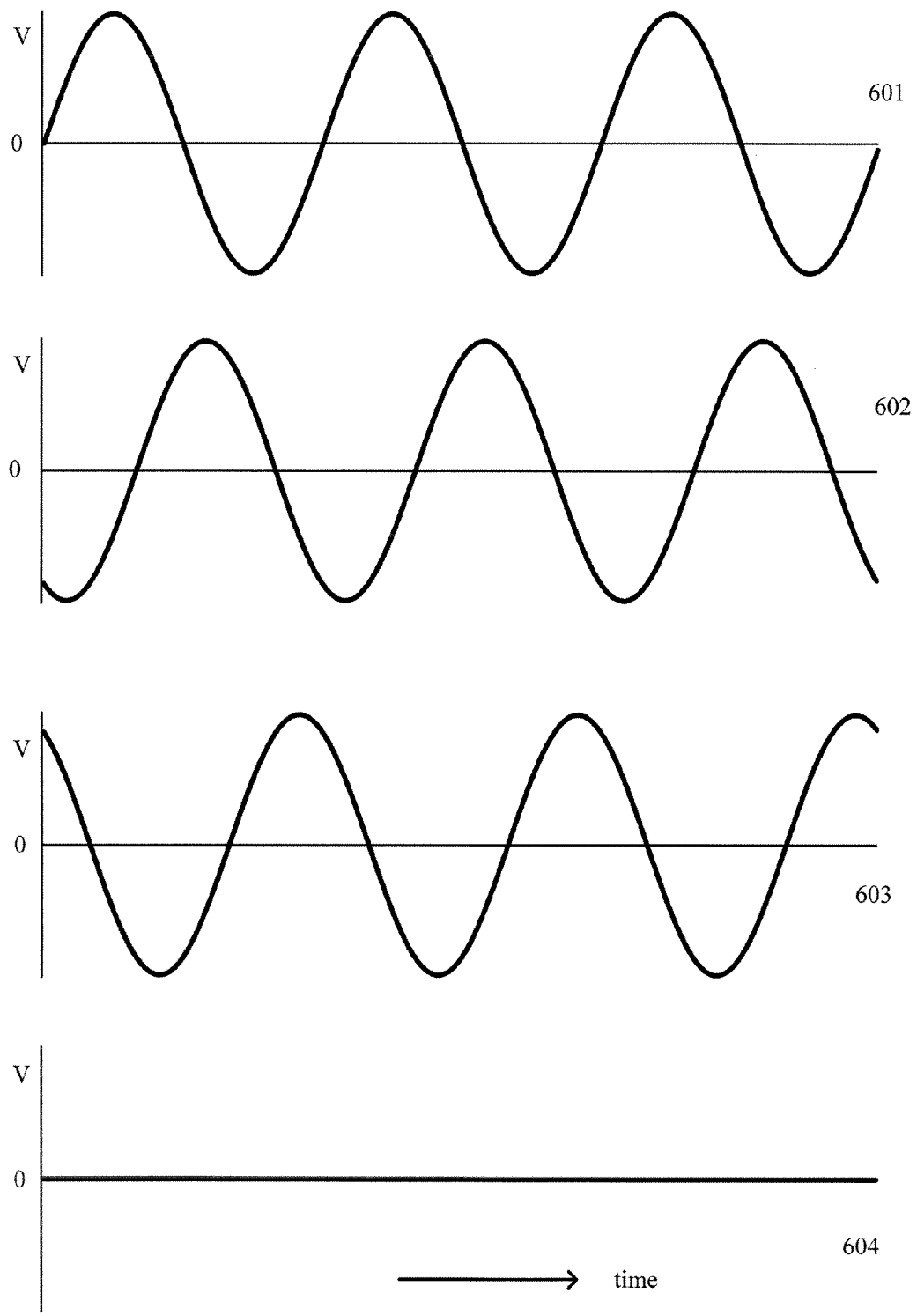
FIG. 6 illustrates exemplary driving waveforms for various signals in the systems, circuits, and methods described herein.

FIG. 6 illustrates exemplary driving voltages for the clock signals of the CCD image sensors. Such clock signals may be generated by the circuits and methods described herein. In a CCD, charge needs to be transferred from one storage element to another until the charge reaches the output amplifier. As explained above, multiple clock signals are needed to transfer the charge. Such clocks are required for embodiments that do not include split-readout image sensors as well as those embodiments including split-readout image sensors. Depending on the design of the CCD, typically 2, 3 or 4 clock signals are needed (or potentially twice those numbers for split-readout CCDs). In preferred embodiments, those clock signals are sinusoidal or substantially sinusoidal. The advantages of using sinusoidal waveforms are that the charge transfer is smoother (which is particularly an advantage in allowing TDI sensors to track the motion of the image more accurately), and the clock signals generate less electrical noise and heat because there is minimal energy in the second and higher harmonics of the fundamental frequency, and because ground return currents are minimized.

FIG. 6 illustrates the clock voltages for a 3-phase CCD. Clock signal 601 shows the voltage on the first clock signal as a function of time. Clock signal 601 is a substantially sinusoidal waveform. The second clock signal 602 also has a voltage that varies as a substantially sinusoidal function of time, but is substantially 120° phase-delayed with respect to clock signal 601. The voltage of the third clock signal 603 also varies a substantially sinusoidal function of time, but is substantially 120° phase-delayed with respect to clock signal 602, and hence substantially 240° phase-delayed with respect to clock signal 601. Line 604 illustrates the sum of the three clock signals 601, 602, and 603, which is substantially zero all the time. The substantially zero sum voltage means that little current from the clock signals flows in the ground signal of the image sensor driven by these clocks, thereby resulting in lower electrical noise levels. This is in contrast to the sum of three out-of-phase square-wave clock signals, which would have a non-zero sum voltage essentially all the time.

In an image sensor including a 2-phase CCD (not shown), the two clock signals would be substantially 180° out of phase with one another. In a 4-phase CCD (not show), the second clock signal would be substantially 90° phase-delayed with respect to the first clock signal, the third clock signal would be substantially 180° phase-delayed with respect to the first clock signal, and the fourth clock signal would be substantially 270° phase-delayed with respect to the first clock signal.

Note that all the above phase values are the optimal phase differences between the clock signals in the image sensor. In accordance with embodiments of the present invention, the clocks may be generated with relative phases that differ from the above values in order to compensate for different path lengths or impedances of the circuits conductors and connections between the drive electronics and the image sensor, such that the clock signals arrive at the active circuits of the image sensor with the desired relative phase relationships.

More details of the use of sinusoidal and other clock signals for driving CCD image sensors can be found in U.S. Pat. Nos. '633 and '309 cited above.

Figure 7A:
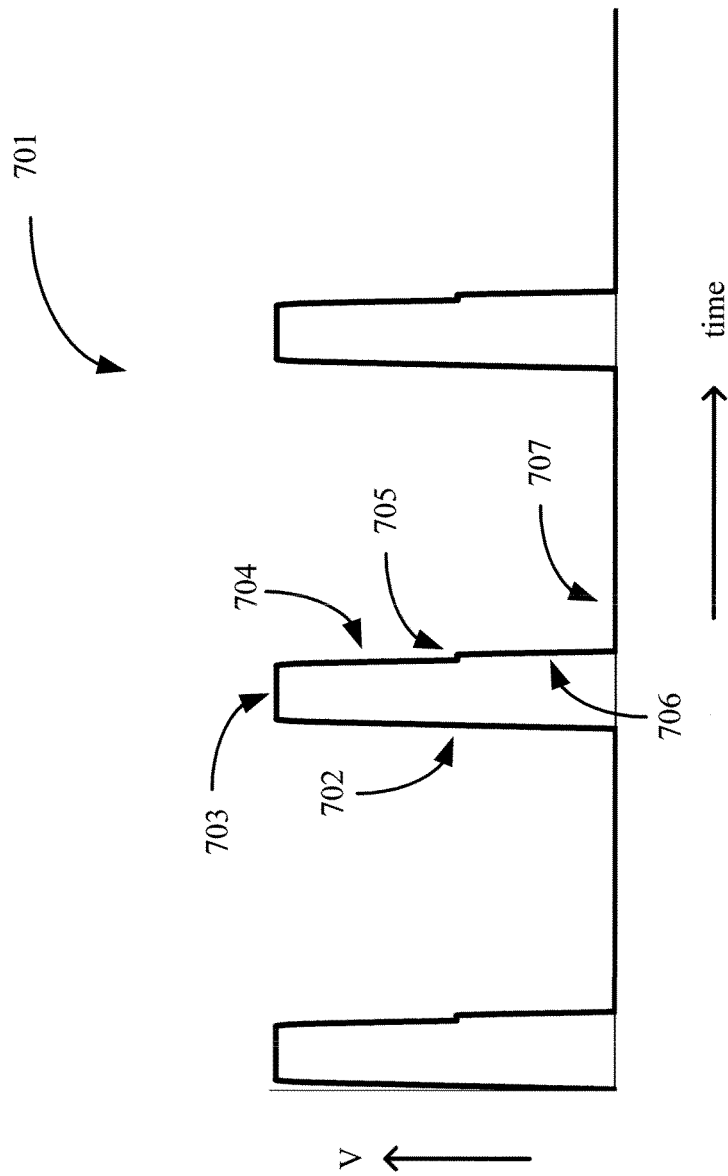
FIG. 7A illustrates an exemplary reset clock waveform generated by a custom waveform generator to improve the settling time of a CCD output signal in accordance with an embodiment described herein.

FIG. 7A illustrates an exemplary voltage waveform 701 that can be used for a reset clock. As explained above, when a CCD is read out at high speed, such as a speed of about 50 MHz or higher, there may not be enough time for the signal to fully settle. In one embodiment of the present invention, a custom waveform generator can be used to generate a reset clock pulse that has a shape that improves the settling time of the output voltage of the CCD. As shown in FIG. 7A, the reset clock pulse may start with a rapid increase in voltage as indicated by arrow 702 with a short rise time. Feed-through from the rising edge of the pulse to the CCD signal is less important than from the falling edge as there is more time for the CCD signal to stabilize relative to the rising edge (see FIG. 11 and its explanation above). Hence, in some embodiments, the rise time can be a few ns or less. The reset clock voltage is then relatively constant at a high level as indicated by arrow 703 (such as approximately +6V to +8V) for long enough to allow the reset transistor to discharge the signal from the previous pixel. The falling edge of the reset clock (as indicated by arrows 704, 705, and 706) can be tailored to reduce the settling time. In the example embodiment of FIG. 7A, the falling edge of the clock first decreases to the voltage level indicated by arrow 705, then pauses for a short time before decreasing back to its low state indicated by arrow 707. The low state indicated by arrow 707 may correspond to a voltage that is approximately zero, or a voltage that is slightly negative, such as a voltage of approximately −1V or −2V. The voltage level indicated by arrow 705 and the time spent at that voltage level are chosen so that the ringing or instability caused by the last part of the falling edge indicated by arrow 706 is approximately 180° out of phase with the ringing or instability caused by first part of the falling edge indicated by arrow 704 but of similar magnitude, so that there is approximate cancellation of the instability caused by the two parts of the falling edge.

Figure 7B:
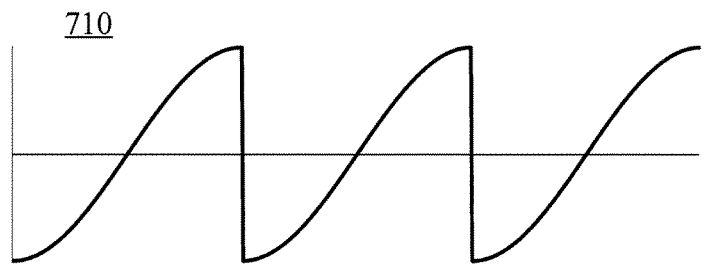
FIGS. 7B, 7C, and 7D illustrate other waveforms that could be generated by the custom waveform generator to optimize the settling time or reduce the noise level of a CCD or other sensor output signal.
Figure 7C:
Figure 7D:
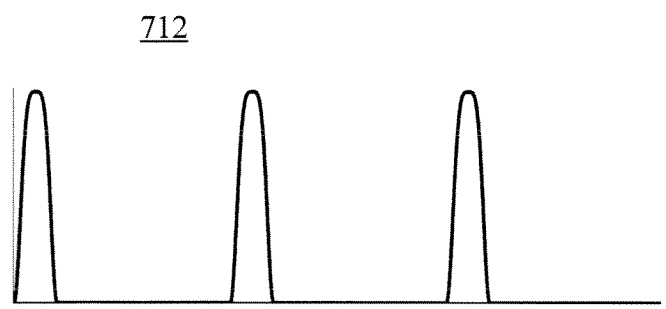
Figure 11:
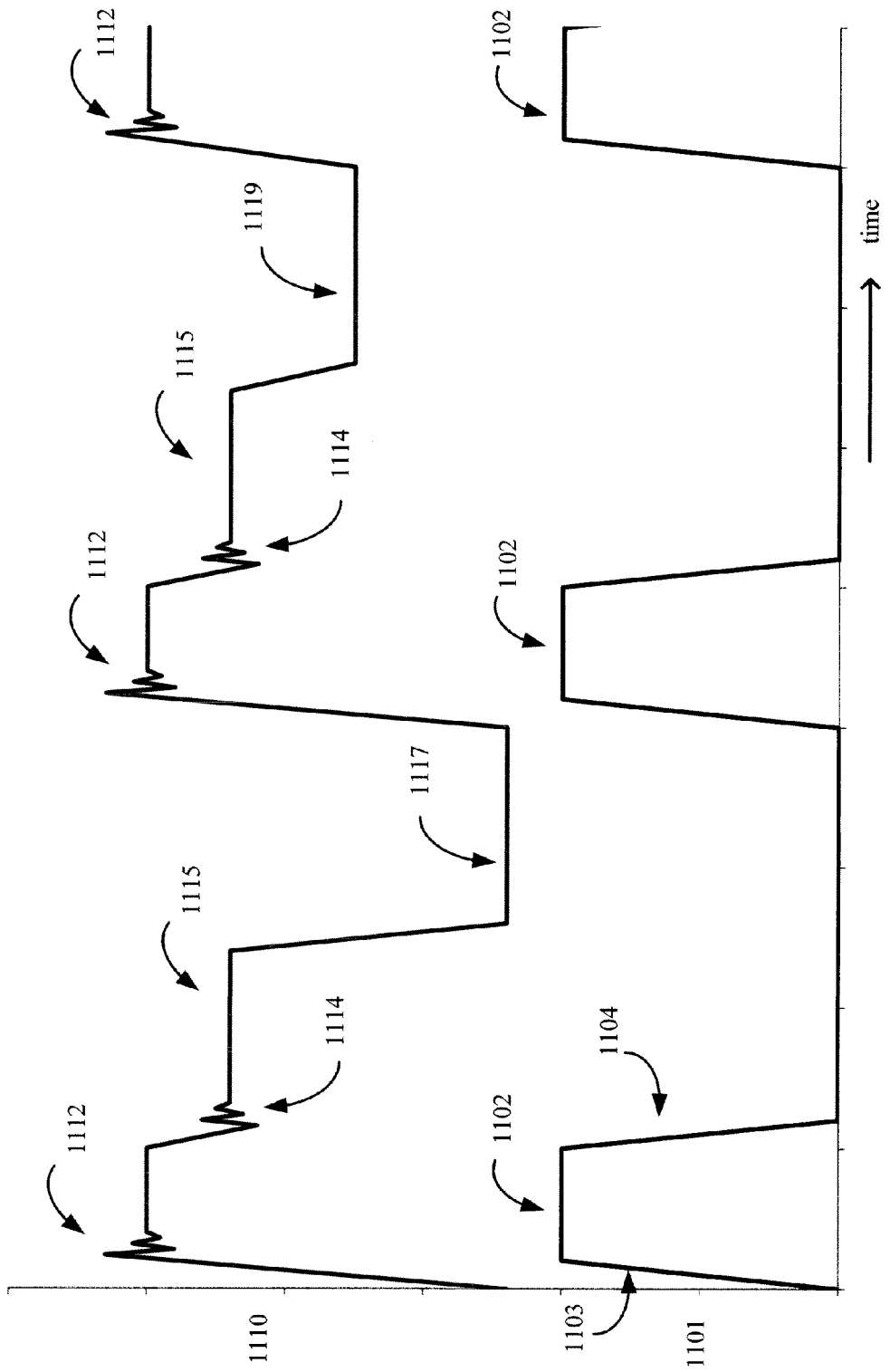
FIG. 11 illustrates typical reset clock and output voltage waveforms for prior art sensors and electronics.

Note that waveform 701 is an illustration of one possible shape for a reset clock pulse that can improve the settling time for instabilities (similar to those indicated by arrow 1114 in FIG. 11). The custom waveform generator, which is described below, is capable of generating different pulse shapes to allow optimization of the settling time of the sensor output signal. One skilled in the appropriate arts would understand that by measuring the response of the sensor output signal to a step function or a short pulse, a reset clock pulse can be designed to reduce instability and provide quicker settling of the sensor signal compared with a simple rectangular or trapezoidal pulse. For example, FIGS. 7B, 7C, and 7D illustrate other waveforms 710-712 that could be generated by the custom waveform generator to optimize the settling time of the sensor output signal or to reduce the noise level on the sensor output signal. Specifically, FIG. 7B illustrates a clock signal that could be used for an output gate, or in an embodiment where there are only two columns per output. FIGS. 7C and 7D illustrate reset clock waveforms that can reduce noise and improve settling time, although perhaps less optimized that the reset clock waveform of FIG. 7A.

Figure 8:
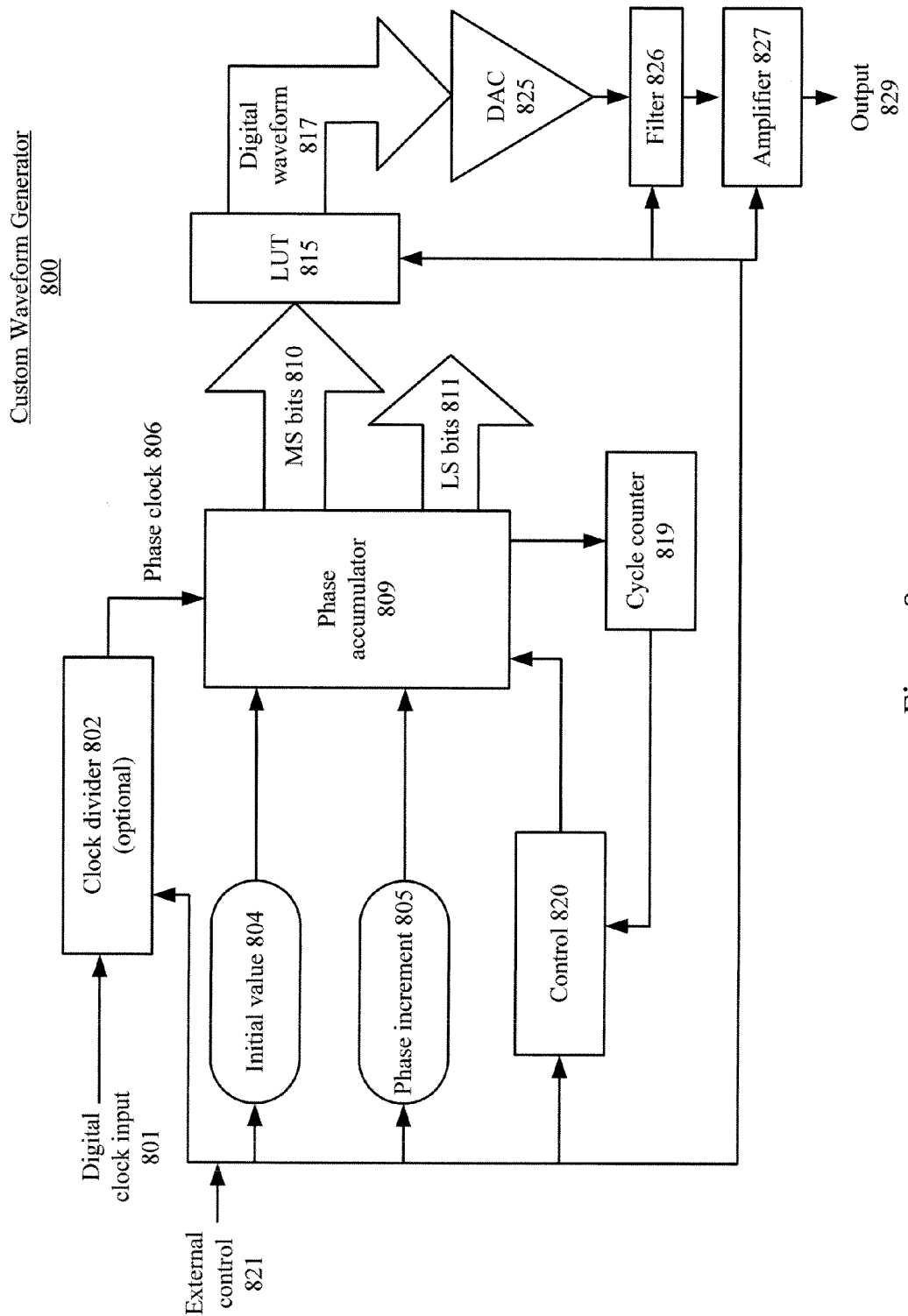
FIG. 8 illustrates an exemplary custom waveform generator that may be used with the systems, circuits, and methods described herein.

FIG. 8 illustrates a block diagram of key aspects of an exemplary custom waveform generator 800 that can generate any of the waveforms described herein. For example, an output 829 of custom waveform generator 800 could be the waveforms described in reference to FIG. 6 or 7A-7F. These waveforms, used for operating an image sensor, can include clock waveforms and reset waveforms. A digital clock input 801 is used as a master clock to control the timing of the internal operation of custom waveform generator 800 and to control the timing of the custom waveform that is generated. Digital clock input 801 may optionally be divided down by a fixed or programmable clock divider 802 to generate a phase clock 806 that may be at the same, or lower, frequency than input clock 801. In some embodiments, clock divider 802 may include a phase-locked loop that generates a frequency for phase clock 806 that is higher than the input clock frequency. Phase clock 806 controls a phase accumulator 809, which together determine the frequency of the generated custom waveform.

Digital values corresponding to the desired custom waveform are loaded into a look-up table (LUT) 815. Look-up table 815 may comprise read-write memory that can be loaded from a computer (not shown), and/or may comprise read-only or non-volatile memory that can be preloaded with the digital values corresponding to one or more waveforms. An exemplary look-up table 815 may comprise 256, 1024, or 65536 memory elements. Although it is convenient for the number of memory elements in look-up table 815 to be equal to a power of 2 (such as $2^8$, $2^{10}$ or $2^{16}$), look-up table 815 could be of any size. The most significant bits of phase accumulator 809 are used as an address to determine which entry in look-up table 815 is output as a digital waveform 817. The number of bits used as the address is determined by the size of the look-up table. For example, if look-up table 815 is 65536 memory elements in size, then the most significant 16 bits of the accumulator will be used as the address for the look-up table.

A digital-to-analog convert (DAC) 825 converts digital waveform 817 to an analog signal. The output voltage from digital-to-analog converter 825 is filtered by a filter 826 to create a smoother waveform, and then amplified by an amplifier 827 to create an output 829 with the desired voltage swing, such as approximately ±6V or ±8V. Amplifier 827 has sufficient current drive to drive the image sensor and any interconnects or circuit board signal traces connecting output 829 to the image sensor. As indicated above, output 829 could include waveforms such as those described in reference to FIGS. 6 and 7A-7D. Exemplary waveforms could include sine waves, slightly distorted sine waves, half-sine waves, pulses, and tailored pulses.

Phase accumulator 809 preferably has more bits than are needed to address look-up table 815 so that extra least significant bits 811 can be used to implement fractional phase changes in each clock cycle to allow more accurate synthesis of waveforms at frequencies that are not simple integer fractions of clock input 801. Other than accumulating a fractional phase shift each clock cycle, least significant bits 811 need not be used elsewhere in custom waveform generator 800. In one embodiment, phase accumulator 809 may comprise 24 bits, of which the 16 most significant bits are used as the address for look-up table 815. In another embodiment, phase accumulator 809 may comprise 32 bits, of which the 16 most significant bits are used as the address for look-up table 815.

When a new waveform needs to be generated, an initial value 804 is loaded into phase accumulator 809 and a cycle counter 819 is set to zero. As explained above, the most significant bits 810 of phase accumulator 809 determine the voltage of output 829 by selecting a specific entry in look-up table 815. Each cycle of phase clock 806 causes phase accumulator 809 to add a phase increment 805 to the current value in the phase accumulator 809. The addition of phase increment 805 to the value in phase accumulator 809 is done modulo the maximum value that the phase accumulator 809 can hold. For example, if phase accumulator 809 is a 24-bit accumulator, then the addition is done modulo 16,777,216 ($2^{24}$). Each time the addition of phase increment 805 causes phase accumulator 809 to overflow, a cycle counter 819 is incremented. For example, if phase accumulator 809 is a 24-bit accumulator, then each time that the addition of phase increment 805 to the value in the phase accumulator 809 would result in a value of 16,777,216 or larger, cycle counter 819 will be incremented. The output of cycle counter 819 can be used to stop custom waveform generator 800 after a required number of cycles of the waveform have been generated. For example, if the custom waveform generator 800 is used to generate a clock waveform for one segment of a CCD output serial register and that serial register segment is 16 pixels long, then custom waveform generator 800 may be programmed to stop after 16 cycles. A control block 820 compares the output of cycle counter 819 with the desired maximum count and generates appropriate control signals to stop the output waveform when that desired maximum count is reached. When a continuous waveform that does not stop is desired, counter 819 can be disabled, or control block 820 can ignore the output value of cycle counter 819, to allow the waveform to run continuously.

An external control 821 can provide overall control of custom waveform generator 800, including such functions as loading values into look-up table 815, setting clock divider 802, setting initial value 804, setting phase increment 805, loading control block 820, and controlling filter 826 and amplifier 827. External control 821 may perform other control functions. External control 821 may interface to a computer through an $I^2C$ bus, USB interface, or any other suitable digital interface.

In one embodiment, all the functions of custom waveform generator 800 can be implemented in a single integrated circuit, such as an application-specific integrated circuit (ASIC). In one embodiment, two or more custom waveform generators can be implemented in a single integrated circuit. In another embodiment, the digital functions (for example, all of the functions except those of DAC 825, filter 826, and amplifier 827) could be implemented in one integrated circuit and the analog functions (such as DAC 825, filter 826, and amplifier 827) could be implemented in another integrated circuit. One key advantage of implementing the custom waveform generator in or two integrated circuits is that it makes it possible to place multiple custom waveform generators close to an image sensor making it easier to ensure that the multiple clock signals required to control that sensor arrive at the sensor with minimal distortion and with minimal cross coupling to other signals. This is particularly important for sensors in semiconductor inspection and metrology systems that are required to run at high speed (such as multiple giga-pixels per second) with low noise. Integrating two or more custom waveform generators in a single integrated circuit allows yet more efficient packing.

Figure 9:
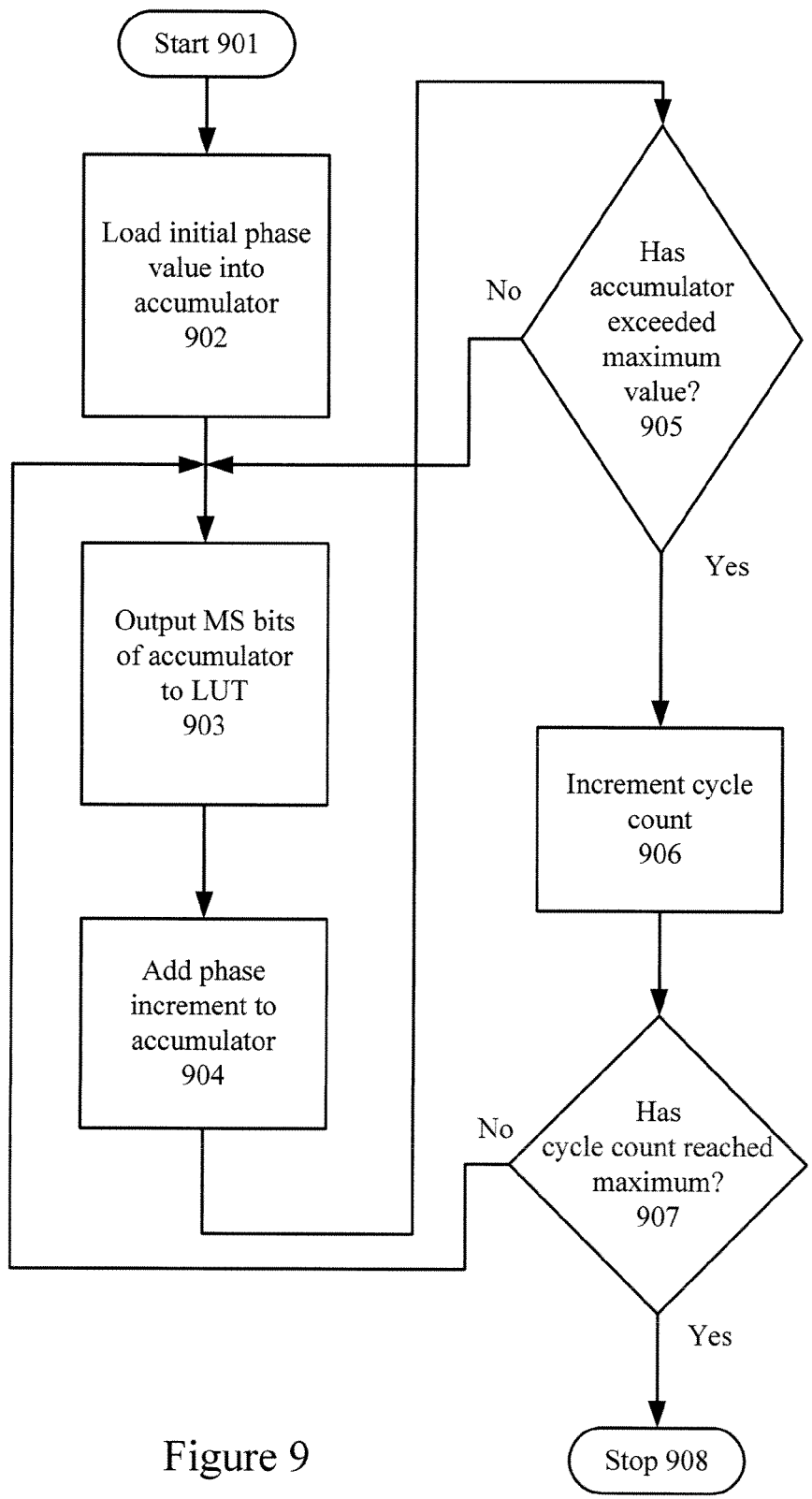
FIG. 9 illustrates an exemplary method of generating a custom waveform that may be used with the systems, circuits, and methods described herein.

FIG. 9 illustrates a flow chart of a method 900 for generating a custom waveform. At step 902, an initial phase value is loaded into the accumulator. At step 903, the most significant bits of the accumulator are output to the look-up table, which in turn outputs the desired digital value of the custom waveform as described above.

On each cycle of the phase clock, the phase increment can be added to the accumulator in step 904. If the accumulator has not exceeded its maximum value, as checked in step 905, then the method will repeat outputting the most significant bits (step 903) and adding the phase increment to the accumulator (step 904). If the maximum value has been exceeded (step 905), then the overflow of the counter will not affect the value of the counter (i.e. the arithmetic is performed modulo the maximum value of the counter plus one), and the cycle count can be incremented in step 906. For example if the phase accumulator has 24 bits, then the maximum value of the accumulator will be 16,777,215 and the arithmetic of adding the phase increment to the accumulator will be performed modulo 16,777,216.

At step 907, the cycle count is checked. If the cycle count has reached its maximum value (for example, a maximum value of 16), then the generation of the custom waveform stops in step 908. Otherwise, the process repeats from step 903. Note that if a continuous waveform is required, then step 907 should loop back to step 903 without doing any check. In such a case, the custom waveform generator will run continuously until some external stop signal is sent.

As explained above for custom waveform generator 800 of FIG. 8, method 900 could be implemented in a single application-specific integrated circuit containing both digital and analog circuits, or in two integrated circuits, one for the digital circuits and another one for the analog circuits.

Figure 10:
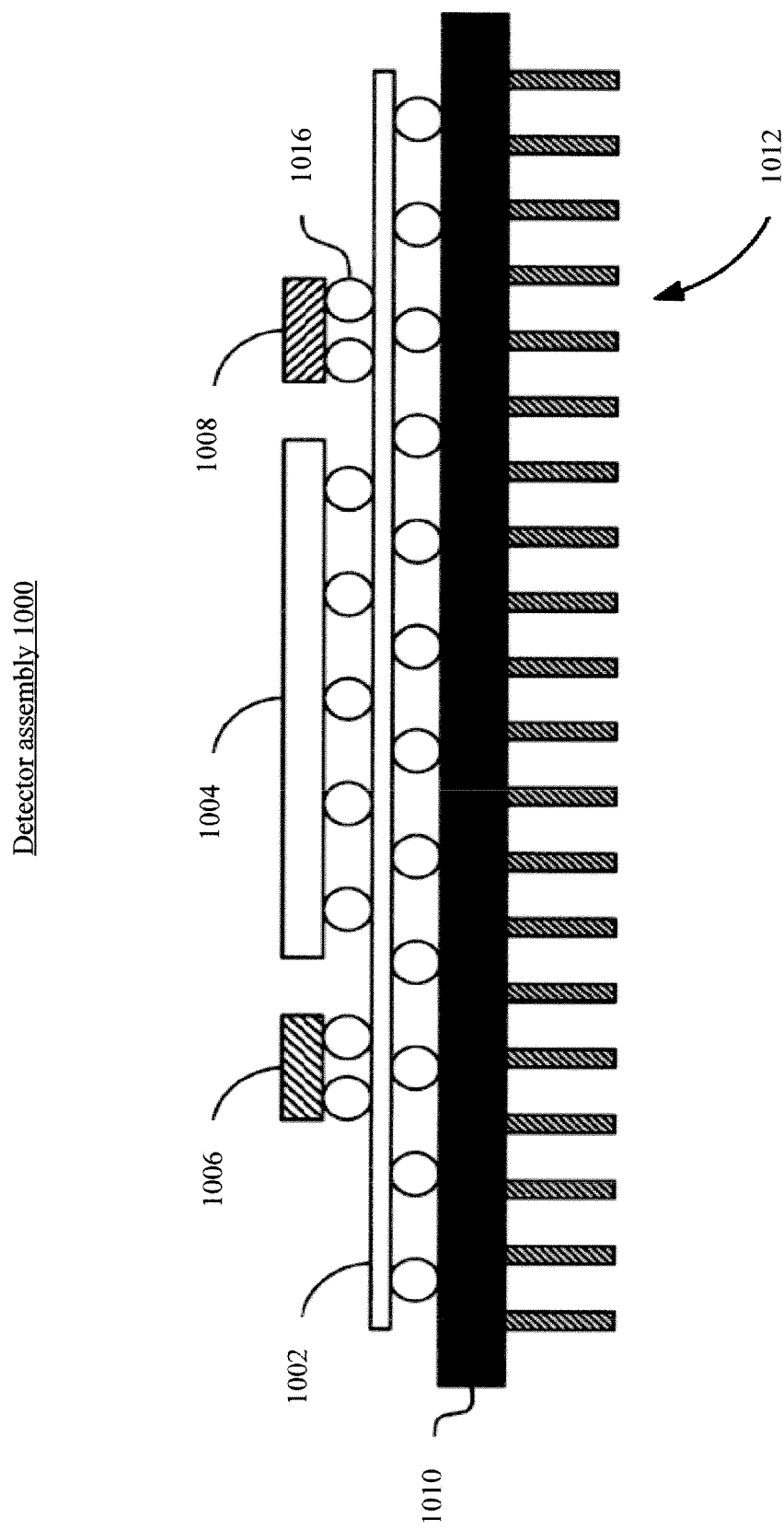
FIG. 10 illustrates an exemplary detector assembly incorporating circuits described herein.

FIG. 10 illustrates an exemplary detector assembly 1000 incorporating an image sensor 1004, an interposer 1002, a driver circuit 1006 (which may include an custom waveform generator), and other electronics in accordance with certain embodiments of the present invention.

In one aspect of the present invention, detector assembly 1000 may include one or more light sensitive sensors 1004 disposed on the surface of interposer 1002. In some embodiments, interposer 1002 of detector assembly 1000 may include, but is not limited to, one or more silicon interposers. In a further aspect of the present invention, the one or more light sensitive sensors 1004 of detector assembly 1000 are back-thinned and illuminated from the back surface (i.e. are mounted front-surface down on the interposer 1002). In one embodiment, the one or more light sensitive sensors 1004 may be configured for operation at deep UV wavelengths or EUV wavelengths by including a boron layer deposited on the back surface.

In another aspect of the present invention, various circuit elements of detector assembly 1000 are disposed on or built into interposer 1002. In one embodiment, one or more amplification circuits (e.g. charge conversion amplifier) (not shown) may be disposed on or built into interposer 1002. In another embodiment, one or more conversion circuits 1008 (e.g. analog-to-digital conversion circuits, or digitizers) may be disposed on or built into interposer 1002. In another embodiment, one or more driver circuits 1006 may be disposed on or built into interposer 1002. For example, the one or more driver circuits 1006 may include a custom waveform generator as described herein. In another embodiment, one or more decoupling capacitors (not shown) may be disposed on or built into interposer 1002. In a further embodiment, one or more serial transmitters (not shown in FIG. 10) maybe disposed on or built into interposer 1002.

In another aspect of the present invention, one or more support structures may be disposed between the bottom surface of light-sensitive array sensor 1004 and the top surface of interposer 1002 to provide physical support to sensor 1004. In one embodiment, a plurality of solder balls 1016 may be disposed between the bottom surface of light-sensitive array sensor 1004 and the top surface of interposer 1002 to provide physical support to sensor 1004. It is recognized herein that while the imaging region of sensor 1004 might not include external electrical connections, the back-thinning of sensor 1004 causes sensor 1004 to become increasingly flexible. As such, solder balls 1016 may be utilized to connect sensor 1004 to interposer 1002 in a manner that reinforces the imaging portion of sensor 1004. In an alternative embodiment, an underfill material may be disposed between the bottom surface of light-sensitive array sensor 1004 and the top surface of interposer 1002 to provide physical support to sensor 1004. For example, an epoxy resin may be disposed between the bottom surface of light-sensitive array sensor 1004 and the top surface of interposer 1002.

In another aspect of the present invention, interposer 1002 and the various additional circuitry (e.g. amplification circuits, driver circuits 1006, digitizer circuits 1008, and the like) are disposed on a surface of a substrate 1010. In a further aspect, substrate 1010 may include a substrate having high thermal conductivity (e.g. a ceramic substrate). In this regard, substrate 1010 may be configured to provide physical support to sensor 1004 and interposer 1002, while also providing a means for detector assembly 1000 to efficiently conduct heat away from imaging sensor 1004 and various other circuitry (e.g. digitizer 1008, driver circuits 1006, amplifier, and the like). Note that substrate 1010 may include any rigid highly heat-conductive substrate material known in the art. For example, substrate 1010 may include, but is not limited to, a ceramic substrate. For instance, substrate 1010 may include, but is not limited to, aluminum nitride. Interposer 1002 may be electrically connected to conductors on substrate 1010 by solder balls, by wire bonds or by other means.

In another embodiment, substrate 1010 may be configured to provide an interface to a socket or an underlying printed circuit board (PCB). For example, as shown in FIG. 10, substrate 1010 may provide interconnection between interposer 1002 and a socket or a PCB via interconnects 1012. Those skilled in the art will recognize that substrate 1010 may be operatively coupled to an underlying PCB and further electrically coupled to a socket or PCB in a variety of ways, all of which are interpreted to be within the scope of the present invention.

More details of detector assemblies incorporating image sensors, interposers, driver circuits and other electronics can be found in U.S. patent application Ser. No. 13/622,155, entitled "Interposer based imaging sensor for high-speed image acquisition and inspection systems", filed on Sep. 18, 2012, and incorporated by reference herein.

The various embodiments of the structures and methods of this invention that are described above are illustrative only of the principles of this invention and are not intended to limit the scope of the invention to the particular embodiments described. For example, additional steps may be added to the flow chart depicted in FIG. 9, or some of the steps shown may be done in different sequence than shown. In another example, custom waveforms different from those depicted in FIGS. 6 and 7A-7D may be generated by the systems and methods described herein in order to reduce the noise level or reduce the settling time of signals from an image sensor. Thus, the invention is limited only by the following claims and their equivalents.

The invention claimed is:

1. A method of inspecting a sample at high speed, the method comprising:
   directing and focusing radiation onto the sample;
   receiving radiation from the sample and directing received radiation to an image sensor; and
   driving the image sensor with predetermined signals, the predetermined signals minimizing a settling time of an output signal of the image sensor, the predetermined signals controlled by a phase accumulator, which is used to select look-up values.

2. The method of claim 1, wherein said driving includes loading an initial phase value into the phase accumulator.

3. The method of claim 2, wherein the look-up values are selected by most significant bits of the phase accumulator.

4. The method of claim 3, wherein said driving includes converting the look-up values to an analog signal.

5. The method of claim 4, wherein said driving includes on each cycle of a phase clock, adding a phase increment to the phase accumulator.

6. The method of claim 5, wherein said driving includes determining whether a maximum phase accumulator value is exceeded.

7. The method of claim 6, wherein said driving includes:
   when the maximum phase accumulator value is not exceeded, selecting the most significant bits of the phase accumulator and said adding the phase increment to the phase accumulator.

8. The method of claim 7, wherein said driving includes:
   when the maximum phase accumulator value is exceeded, then incrementing a cycle count.

9. The method of claim 8, wherein said driving includes determining whether a maximum count cycle value is exceeded.

10. The method of claim 9, wherein said driving includes:
    when the maximum count cycle value is not exceeded, then repeating said selecting the most significant bits of the phase accumulator and said adding the phase increment to the phase accumulator.

11. The method of claim 10, wherein said driving includes:
    when the maximum count cycle value is exceeded, then stopping said driving.

12. The method of claim 3, wherein the most significant bits are 16 bits.

13. The method of claim 1, wherein the received radiation is scattered radiation.

14. The method of claim 1, wherein the received radiation is reflected radiation.

15. A system for inspecting a sample, the system comprising:
    an illumination source;
    a device configured to perform light detection;
    optics configured to direct light from the illumination source to the sample and to direct light outputs, reflections, or transmissions from the sample to the device;
    a driving circuit for driving the device, the driving circuit comprising a custom waveform generator that minimizes a settling time of an output signal of the device, the custom waveform generator including a phase accumulator for receiving clock and control signals, a look-up table coupled to an output of the phase accumulator, and a digital-to-analog converter coupled to an output of the look-up table.

16. The system of claim 15, wherein the optics includes:
    a first channel image mode relay when the light outputs, reflections, or transmissions correspond to a first channel; and
    a second channel image mode relay when the light outputs, reflections, or transmissions correspond to a second channel,
    wherein the device is an image sensor configured to receive relay outputs of the first channel image mode relay and the second channel image mode relay.

17. The system of claim 15, wherein the device comprises a semiconductor membrane, the semiconductor membrane including circuit elements formed on a first surface of the semiconductor membrane and a pure boron layer deposited on a second surface of the semiconductor membrane.

18. The system of claim 15, wherein the device comprises two sets of readout circuits positioned on either side of an image region.

19. The system of claim 15, wherein the device comprises an electron bombarded image sensor.

20. The system of claim 15, wherein the device includes one or more image sensors.

* * * * *